United States Patent
Draghici et al.

(10) Patent No.: US 10,248,757 B2
(45) Date of Patent: Apr. 2, 2019

(54) GENETIC, METABOLIC AND BIOCHEMICAL PATHWAY ANALYSIS SYSTEM AND METHODS

(71) Applicant: Wayne State University, Detroit, MI (US)

(72) Inventors: Sorin Draghici, Detroit, MI (US); Zhonghui Xu, Detroit, MI (US); Michele Donato, Detroit, MI (US)

(73) Assignee: WAYNE STATE UNIVERSITY, Detroit, MI (US)

(*) Notice: Subject to any disclaimer, the term of this patent is extended or adjusted under 35 U.S.C. 154(b) by 1310 days.

(21) Appl. No.: 14/103,259

(22) Filed: Dec. 11, 2013

(65) Prior Publication Data

US 2014/0172385 A1 Jun. 19, 2014

Related U.S. Application Data

(60) Provisional application No. 61/735,732, filed on Dec. 11, 2012.

(51) Int. Cl.
| | |
|---|---|
| G06F 7/60 | (2006.01) |
| G06F 17/10 | (2006.01) |
| G06F 19/12 | (2011.01) |
| G06F 17/50 | (2006.01) |
| G06F 19/18 | (2011.01) |

(52) U.S. Cl.
CPC .............. *G06F 19/12* (2013.01); *G06F 17/50* (2013.01); *G06F 19/18* (2013.01)

(58) Field of Classification Search
None
See application file for complete search history.

(56) References Cited

U.S. PATENT DOCUMENTS

| | | | |
|---|---|---|---|
| 8,068,994 | B2 | 11/2011 | Draghici |
| 2014/0172384 | A1 | 6/2014 | Draghici et al. |

OTHER PUBLICATIONS

Donato, Michele et al., "A Method for Analysis and Correction of Cross-Talk Effects in Pathway Analysis", Jun. 10-15, 2012, WCCI 2012 IEEE World Congress on Computational Intelligence, IEEE.*
Gfeller, David et al., "The Multiple-Specificity Landscape of Modular Peptide Recognition Domains", 2011, Molecular Systems Biology 7, Article No. 484, EMBO and Macmillan Publishers Limited.*

(Continued)

*Primary Examiner* — Cedric Johnson
(74) *Attorney, Agent, or Firm* — Harness, Dickey & Pierce, P.L.C.

(57) ABSTRACT

Identifying pathways that are significantly impacted in a given condition is a crucial step in the understanding of the underlying biological phenomena. All approaches currently available for this purpose calculate a p-value that aims to quantify the significance of the involvement of each pathway in the given phenotype. These p-values were previously thought to be independent. Here, we show that this is not the case, and that pathways can affect each other's p-values through a "crosstalk" phenomenon that affects all major categories of existing methods. We describe a novel technique able to detect, quantify, and correct crosstalk effects, as well as identify novel independent functional modules. We assessed this technique on data from four real experiments coming from three phenotypes involving two species.

3 Claims, 19 Drawing Sheets

(56) References Cited

OTHER PUBLICATIONS

Donato, Michele et al., "Signaling Pathways Coupling Phenomena", 2010, IEEE.*
Ravcheev, Dmitry A. et al., "Inference of the Transcriptional Regulatory Network in *Staphylocossus aureus* by Integration of Experimental and Genomics-Based Evidence", Jul. 2011, Journal of Bacteriology, vol. 193, No. 13, American Society for Microbiology.*
Alberts et al. "Molecular biology of the cell 4th edition." Garland Science (2002).
Al-Shahrour et al. FatiGO: a web tool for finding significant associations of Gene Ontology terms with groups of genes. Bioinformatics, 20(4):578-580 (2004).
Amaral et al. "Angiotensin II and VEGF are involved in angiogenesis induced by short-term exercise training," American Journal Of Physiology-Heart And Circulatory Physiology, 281(3):H1163-H1169, Sep. 2001.
Ashburner et al. "Gene ontology: tool for the unification of biology," Nature Genetics, vol. 25, pp. 25-29 (2000).
Beissbarth et al. GOstat: find statistically overrepresented gene ontologies wtihin a group of genes. Bioinformatics., 20:1464-1465, Jun. 2004.
Berriz et al. "Characterizing gene sets with FuncAssociate." Bioinformatics, 19(18):2502-2504, 2003.
Berry et al. "Mammary localization and abundance of laminin, fibronectin, and collagen IV proteins in prepubertal heifers." Jouranl of Dairy Science 86, 2864-74 (2003).
BioCarta, "BioCarta-Charting Pathways of Life," http://www. biocarta.com.
Bishop "Pelvic Scoring for Elective Induction." Obstetrics and Gynecology 24, 266-268 (1964).
Campbell et al. "Estrogens for menopausal flushing." British Medical Journal 1, 104-105 (1977).
Cardona-Gomez et al. "Estradiol inhibits GSK3 and regulates interaction of estrogen receptors, GSK3, and beta-catenin in the hippocampus." Molecular and Cellular Neuroscience 25, 363-73 (2004).
Castillo-Davis et al. "GeneMerge-post-genomic analysis, data mining, and hypothesis testing." Bioinformatics, 19(7):891-892, May 2003.
Chlebowski et al. "Lung cancer among postmenopausal women treated with estrogen alone in the women's health initiative randomized trial." Journal of the National Cancer Institute 102, 1143-1421 (2010).
Chlebowski et al. "Non-small cell lung cancer and estrogen plus progestin use in post-menopausal women in the Women's Health Initiative randomized clinical trial." Journal of Clinical Oncology 27(18): CRA1500—ASCO Meeting Abstracts (2009).
Chlebowski et al. "Oestrogen plus progestin and lung cancer in postmenopausal women (women's health initiative trial): a post-hoc analysis of randomised controlled trial." Lancet 374, 1243-1251 (2009).
Dennis et al. "DAVID: Database for annotation, visualization, and integrated discovery." Genome Biology, 4:P3 (2003).
Donato et al. "Analysis and correction of crosstalk effects in pathway analysis." Genome research 23.11 (2013): 1885-1893.
Donato, et al. "Singaling pathways coupling phenomena." Neural Networks (IJCNN), the 2010 International Joint Conference on IEEE (2010).
Draghici et al. "Global functional profiling of gene expression," Genomics, vol. 81, No. 2, pp. 98-104, Feb. 2003.
Draghici et al. "A systems biology approach for pathway level analysis." Genome Research, 17(10):1537-1545, (2007).
Edgar et al. "Gene expression omnibus: Ncbi gene expression and hybridization array data repository," Nucleic acids research, vol. 30, No. 1, pp. 207-210 (2002).
Fabel et al. "VEGF is necessary for exercise-induced adult hippocampal neurogenesis." European Journal Of Neuroscience, 18(10):2803-2812, Nov. 2003.
Fukata et al. "Role of toll-like receptors in gastrointestinal malignancies," Oncogene, vol. 27, No. 2, pp. 234-243 (2008).
Granneman et al. "Metabolic and cellular plasticity in white adipose tissue i: effects of beta3-adrenergic receptor activation," American Journal Of Physiology-Endocrinology And Metabolism, vol. 289, No. 4, pp. E608-E616 (2005).
Han et al. "Mutation of the androgen receptor causes oncogenic transformation of the prostate." PNAS 102, 1151-6 (2005).
Hanifi-Moghaddam et al. "Molecular analysis of human endometrium: short-term tibolone signaling differs significantly from estrogen and estrogen plus progestagen signaling." Journal of Molecular Medicine 85, 471-480 (2007).
Hassan et al. "The molecular basis for sonographic cervical shortening at term: identification of differentially expressed genes and the epithelial-mesenchymal transition as a function of cervical length." American Journal of Obsteric and Gynecology 203, 472el-472.e14 (2010).
Hassan et al. "The transciptome of the uterine cervix before and after spontaneous term parturition." American Journal of Obstetrics and Gynecology 195:778-786 (2006).
Hassan et al. "The transcriptome of cervical ripening in human pregnancy before the onset of labor at term: Identification of novel molecular functions involved in this process." The Journal of Maternal-Fetal and Neonatal Medicine 22, 1183-1193 (2009).
Henderson et al. "Estrogen use and cardiovascular disease." American Journal of Obstetrics and Gynecology 154, 1181-1186 (1986).
Hong et al. "A susceptibility gene set for early onset colorectal cancer that integrates diverse signaling pathways: implication for tumorigenesis." Clinical Cancer Research, vol. 13, No. 4, pp. 1107-1114 (2007).
Hosack et al. "Identifying biological themes within lists of genes with EASE." Genome Biology, 4(6): P4 (2003).
http://www.bioconductor.org.
Hussain et al. "p53 Biological Network: at the crossroads of the cellular-stress response pathway and molecular carcinogenesis." Journal of Nihon Medical School 73, 54-64 (2006).
Joshi-Tope et al. "Reactome: a knowledgebase of biological pathways." Nucleic Acids Research, 33: D428-432 (2005).
Kanehisa et al. "The KEGG resource for deciphering the genome." Nucleic Acids Research, vol. 32 (suppl 1), pp. 277-280, Jan. 2004.
Khatri et al. "Ontological analysis of gene expression data: current tools, limitations, and open problems," Bioinformatics, vol. 21, No. 18, pp. 3587-3595 (2005).
Khatri et al. "Profiling gene expression using Onto-Express," Genomics, vol. 79, No. 2, pp. 266-270, Feb. 2002.
Klessner et al. "EGFR and ADAMs cooperate to regulate shedding and endocytic trafficking of the desmosomal cadherin desmoglein 2." Molecular Biology of the Cell 20, 328-337 (2009).
Kouzmenko et al. "Wnt/beta-catenin and estrogen signaling converge in vivo." Journal of Biological Chemistry 279, 40255-8 (2004).
Lee et al. "In vivo identification of bipotential adipocyte progenitors recruited by Beta3-adrenoceptor activation and high-fat feeding." Cell Metabolism 15, 480-491 (2012).
Leppert "Anatomy and physiology of cervical ripening." Clinical Obstetrics and Gynecology 38, 267-279 (1995).
Leppert et al. "Orientation of elastic fibers in the human cervix." American Journal of Obstetrics and Gynecology 155, 219-224 (1986).
Leung et al. "Estrogen inhibits GH signaling by suppressing GH-induced JAK2 phosphorylation, an effect mediated by SOCS-2." PNAS 100, 1016-1021 (2003).
Li et al. "An essential role of the nf-b/toll-like receptor pathway in induction of inflammatory and tissue-repair gene expression by necrotic cells," The Journal of Immunology, vol. 166, No. 12, pp. 7128-7135 (2001).
Li et al. "Metabolic and cellular plasticity in white adipose tissue ii: tole of peroximose proliferator-activated receptor-alpha," American Journal Of Physiology-Endocrinology And Metabolism, vol. 289, No. 4, pp. E617-E626 (2005).
Mahendroo et al. "The parturition defect in steroid 5alpha-reductase type 1 knockout mice is due to impaired cervical ripening," Molecular Endocrinology 13, 981-992 (1999).

(56) References Cited

OTHER PUBLICATIONS

Martin et al. "GOToolBox: funcational analysis of gene datasets based on gene ontology." Genome Biology, 5:R101 (2004).
Milkiewicz et al. "Association between shear stress, angiogenesis, and VEGF in skeletal muscles in vivo." Microcirculation, 8(4):229-241, Aug. 2001.
Million et al. "Modulation of human breast cancer cell adhesion by estrogens and antiestrogens." Clinical and Experimental Metastasis 7, 405-415 (1989).
Mootha et al. "PGC-1 alpha-responsive genes involved in oxidative phosphorylation are coordinately down regulated in human diabetes," Nature Genetics, vol. 34, No. 3, pp. 267-273, Jul. 2003.
Mottillo et al. "Role of hormonesensitive lipase in beta-adrenergic remodeling of white adipose tissue." American Journal of Physiology, Endocrinology and Metabolism, vol. 293, No. 5, pp. E1188-E1197 (2007).
Naito et al. "Phosphatidylinositol 3-kinase-Akt pathway plays a criticial role in early cardiomyogenesis by regulatin canonical Wnt signaling." Ciriculation Research 97, 144-51 (2005).
Nelson et al. "Postmenopausal hormone replacement therapy—scientific review." Journal of the American Medical Assocation 288, 872-881 (2002).
Newman et al. "Phagocytosis of senescent netrophils by human monocyte-derived macrophages and rabbit inflammatory macrophags." The Journal of Experimental Medicine 156, 430 (1982).
Novaro et al. "Collagen-IV and laminin-1 regulate estrogen receptor alpha expression and function in mouse mammary epithelial cells." Journal of Cell Science 116, 2975-86 (2003).
Pan et al. "Effects of threshold choice on biological conclusions reached during analysis of gene expression by DNA microarrays." Proceedings of the National Academy of Sciences USA, vol. 102, No. 25, pp. 8961-8965 (2005).
Peterziel et al. "Rapid signaling by androgen receptor in prostate cancer cells." Oncogene 18, 6322-9 (1999).
R. D. C. Team, R: A language and enviroment for statistical computing, R Foundation for Statistical Computing, Vienna, Austria, 2005, ISBN 3-900051-07-0.
Rahenführer , "Calculation the statistical significance of changes in pathway activity from gene expression data." Statistical Applications in Genetics and Molecular Biology, 3(1) (2004).
Rossi et al. "The biology of chemokines and their receptors," Annual Review Of Immunology, vol. 18, pp. 217-243 (2000).
Senger et al. "Vascular-Permeabililty Factor (VPF, VEGF) In Tumor Biology." Cancer And Metastasis Reviews, 12(3-4):303-324, Sep. 1993.
Shah et al. "CLENCH: a program for calculating cluster enrichment using the gene ontology." Bioinformatics., 20(7):1196-197, May 2004.
Shureiqi et al. "The 15-lipoxygenase-1 product 13-shydroxyoctadecadienoicacid down-regulates ppar- to induce apoptosis in colorectal cancer cells," Proceedings of the National Academy of Sciences, vol. 100, No. 17, pp. 9968-9973 (2003).

Subramanian et al. "Gene set enrichment analysis: A knowledge-based approach for interpreting genome-wide expression profiles," Proceeding of The National Academy of Sciences of the USA, vol. 102, No. 43,pp. 15 545-15 550 (2005).
Tarca et al. "A novel signaling pathway impact analysis (SPIA)," Bioinformatics, vol. 25, No. 1, pp. 75-82 (2009).
Tarca et al. "Down weighting overlapping genes improved gene set analysis." BMC bioinformatics, vol. 13, No. 136, Jan. 2012.
Tavazoie et al. "Systematic determination of genetic network architecture." Nature Genetics 22, 281-285 (1999).
The Million Women Study. http://millionwomenstudy.org/.
The Women Health Initiative. http://nhlbi.nih.gov/whi/.
Tian et al. "Discovering statistically significant pathways in expression profiling studies," Proceeding of The National Academy of Sciences of the USA, vol. 102, No. 38,pp. 13 544-13 549, (2005).
Timmons et al. "Temporal changes in myeloid cells in the cervix during pregnancy and parturition." Journal of Immunology 182, 2700-2707 (2009).
Uldbjerg et al. "Ripening of the human uterine cervix related to changes in collagen, glycosaminoglycans, and collagenolytic activity." American Journal of Obstetric and Gynecology 147, 662-666 (1983).
Uldbjerg et al. "The ripening of the human uterine cervix in terms of connective tissue biochemistry." Clinical Obstetrics and Gynecology 195, 778-786 (2006).
Voichita et al. "Incorporating gene significance in the impact analysis of signaling pathways." Machine Learning and Application (ICMLA), 2012 11th International Conference on. vol. 1, IEEE (2012).
Wang et al. "High expression of toll-like receptor 4/myeloid differentiation factor 88 signals correlates with poor prognosis in colorectal cancer," British journal of cancer, vol. 102, No. 5, pp. 908-915 (2010).
Weiss et al. "Decreased risk of fractures of the hip and lower forearm with post-menopausal use of estrogen." New England Journal of Medicine 303, 1195-1198 (1980).
Wong et al. "Estrogen receptor interacting protein that modulates its nongenomic activity-crosstalk with Src/Erk phosphorylation cascade." PNAS 99, 14783-8 (2002).
Word et al. "Dynamics of cervical remodeling during pregnancy and parturition: mechanisms and current concepts." Seminars in reproductive medicine 25, 69-79 (2007).
Young et al. Ontologytraverser: an R package for GO analysis. Bioinformatics, 21(2):275-6 (2005).
Zeeberg et al. "Gominer: a resource for biological interpretation of genomic and proteomic data." Genome Biology, 4(4):R28 (2003).
Zhang et al. "MAPK singal pathways in the regulation of cell proliferation in mammalian cells." Cell Research 12, 9-18 (2002).
Zhong et al. "Comparative analysis of gene sets in the gene ontology space under the multiple hypothesis testing frame work." Proc IEEE Comp Systems Bioinformatics, pp. 425-435 (2004).
Ziel "Estrogens role in endometrial cancer" Obstetrics and Gynecology 60, 509-515 (1982).

* cited by examiner

| rank | pathway | pval (fdr) |
|---|---|---|
| 1 | Parkinson's disease | 2.0e-06 |
| 2 | Alzheimer's disease | 3.6e-06 |
| 3 | Huntington's disease | 3.44e-05 |
| 4 | Leishmaniasis | 0.0003 |
| 5 | Phagosome | 0.0006 |
| 6 | Cell cycle | 0.0011 |
| 7 | Oocyte meiosis | 0.0016 |
| 8 | Cardiac muscle contraction | 0.0016 |
| 9 | Toll-like receptor | 0.0018 |
| 10 | PPAR signaling pathway | 0.0018 |
| 11 | Chemokine signaling pathway | 0.0018 |
| 12 | Lysosome | 0.0211 |
| 13 | B cell receptor | 0.0252 |
| 14 | Systemic lupus erythematosus | 0.0292 |
| 15 | Compl. and coag. cascades | 0.0342 |
| 16 | Cytokine-cytokine rec. inter. | 0.0342 |
| 17 | Chagas disease | 0.0466 |
| 18 | Progest. med. oocyte matur. | 0.0530 |
| 19 | Fc epsilon RI signaling pathway | 0.0548 |
| 20 | Leukocyte transendoth migr. | 0.0548 |

-0.01 threshold
-0.05 threshold

Fig. 1a

| rank | pathway | p(fdr) |
|---|---|---|
| 1 | Mitochondrial Activity | 8.13-10 |
| 2 | Phagosome | 9.3e-09 |
| 3 | Cellcycl+Oocyteme | 5.8e-08 |
| 4 | PPAR signaling pathway | 0.001 |
| 5 | Compl. C.C.+Systemic L.E. | 0.002 |
| 6 | *Cytok.-cytok. rec. int. | 0.043 |
| 7 | Toll-like receptor signaling | 0.051 |
| 8 | MAPK signaling pathway | 0.115 |
| 9 | B-cell receptor signaling | 0.145 |
| 10 | Lysome | 0.187 |
| 11 | Nat. killer cell med. cytotox | 0.187 |
| 12 | *Cell cycle | 0.229 |
| 13 | Calcium signaling pathway | 0.229 |
| 14 | Cell adhesion molecules | 0.258 |
| 15 | NOD-like receptor signaling | 0.258 |
| 16 | Vasc. smooth muscle contr. | 0.424 |
| 17 | Dilated cardiomyopathy | 0.424 |
| 18 | *Oocyte meiosis | 0.432 |
| 19 | Type I diabetes mellitus | 0.432 |
| 20 | Wnt signaling pathway | 0.476 |

-0.01 threshold
-0.05 threshold

Fig. 1b

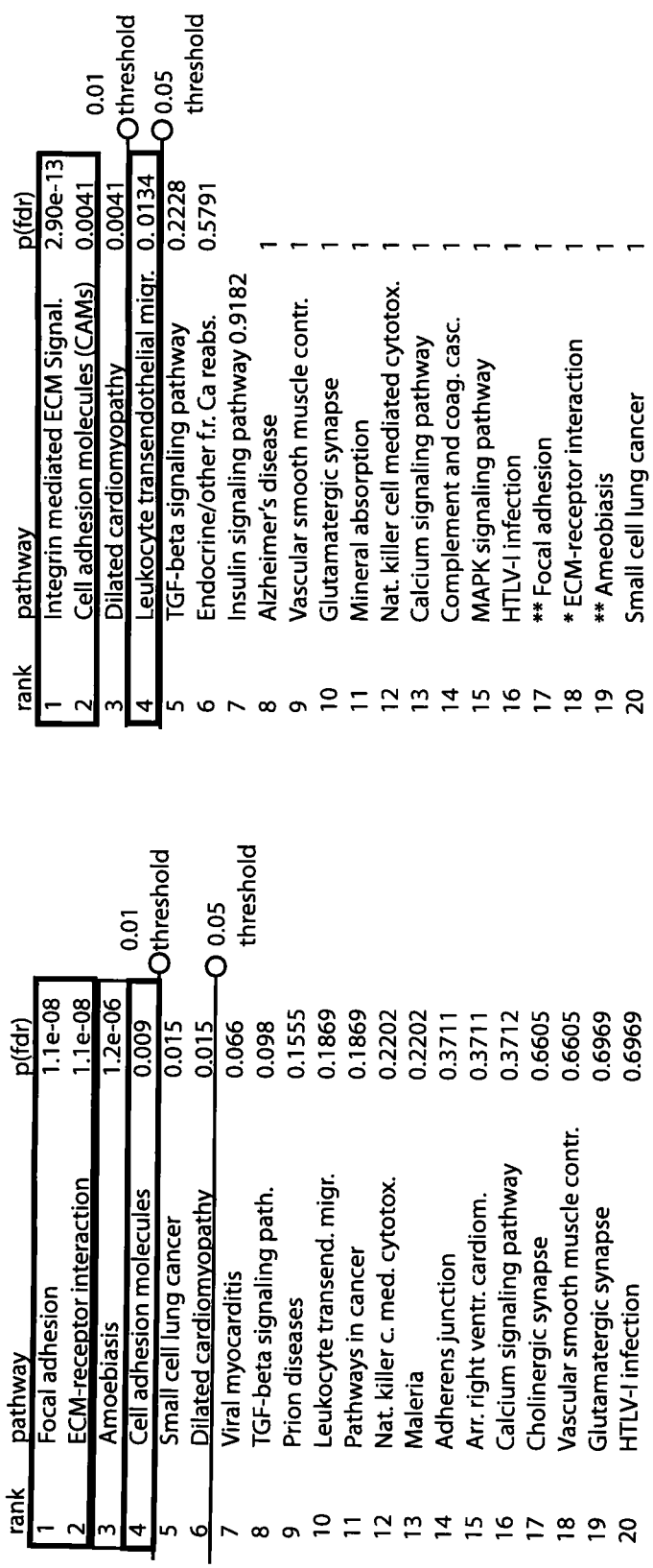

Fig. 7a

|  | DE | NDE | Total |
|---|---|---|---|
| $P_i$ | $n_i$ | $m_i$ | $n_i + m_i$ |
| $P_i^C$ | $n - n_i$ | $m - m_i$ | $(n+m) - (n_i + m_i)$ |
| Total | $n$ | $m$ | $n + m$ |

Fig. 7b

|  | DE | NDE | Total |
|---|---|---|---|
| $P_{i/j}$ | $n_{i/j}$ | $m_{i/j}$ | $n_{i/j} + m_{i/j}$ |
| $(P_{i/j})^C$ | $n - n_{i/j}$ | $m - m_{i/j}$ | $(n+m) - (n_{i/j} + m_{i/j})$ |
| Total | $n$ | $m$ | $n + m$ |

Fig. 9

| rank | pathway | p(FDR) |
|---|---|---|
| 4 | Cell cycle | 0.00044 |
| 6 | p53 signaling pathway | 0.0134 |
| 7 | PPAR signaling pathway | 0.0723 |
| 8 | Gap junction | 0.0920 |
| 9 | Progest. mediated oocyte matur. | 0.0995 |
| 10 | Oocyte meiosis | 0.1327 |
| 11 | Salivary secretion | 0.1442 |
| 12 | Cell adhesion molecules (CAMs) | 0.2390 |
| 13 | SNARE inter. in vesicular transp. | 0.2969 |
| 14 | Prostate cancer | 0.3837 |
| 15 | Vasopressin-reg. water reabs. | 0.5111 |
| 16 | Arrhythm. right ventr. card. | 0.5111 |
| 17 | Hedgehog signaling pathway | 0.5174 |
| 18 | Prion diseases | 0.5420 |
| 19 | Melanogenesis | 0.5432 |
| 20 | Pathways in cancer | 0.5432 |

Fig. 14a

| rank | pathway | p(FDR) |
|---|---|---|
| 1 | Mitochondrial Activity | 2.3e-08 |
| 3 | Cell cycle | 0.001 |
| 4 | PPAR signaling pathway | 0.015 |
| 5 | Cell adhesion molecules (CAMs) | 0.019 |
| 7 | Vascular smooth muscle contr. | 0.080 |
| 8 | p53 signaling pathway | 0.125 |
| 9 | Pathways in cancer | 0.562 |
| 10 | SNARE inter. in vesicular transp. | 0.562 |
| 11 | Chagas disease | 0.575 |
| 12 | Long-term potentiation | 0.575 |
| 13 | Phagosome | 0.588 |
| 14 | Vasopressin-reg. water reabs. | 0.765 |
| 15 | Hedgehog signaling pathway | 0.765 |
| 16 | Dorso-ventral axis formation | 0.765 |
| 17 | Intest. imm. netw. for IgA prod. | 0.784 |
| 18 | Wnt signaling pathway | 0.984 |
| 19 | ECM-receptor interaction | 0.984 |
| 20 | Phototransduction | 0.984 |

Fig. 14b

| rank | pathway | p(FDR) |
|---|---|---|
| 1 | ECM-rec. interaction | 0.0343 |
| 2 | Focal adhesion | 0.0401 |
| 3 | Pathways in cancer | 0.0401 |
| 4 | | |
| 5 | Axon guidance | 0.0401 |
| 6 | | |
| 7 | Jak-STAT signaling pathway | 0.0401 |
| 8 | Progest.-med. oocyte mat. | 0.0951 |
| 9 | Adipocytokine signaling | 0.0951 |
| 10 | Melanoma | 0.1208 |
| 11 | Graft-versus-host disease | 0.1291 |
| 12 | Reg. of actin cytoskeleton | 0.2020 |
| 13 | Aldosterone-reg. Na reabs. | 0.2020 |
| 14 | Oocyte meiosis | 0.2168 |
| 15 | Long-term depression | 0.2174 |
| 16 | mTOR signaling pathway | 0.3048 |
| 17 | Nat. killer cell med. cytotox. | 0.3185 |
| 18 | Vibrio cholerae infection | 0.3225 |
| 19 | SNARE inter. in vesicular trans. | 0.3699 |
| 20 | Salivary secretion | 0.3699 |

Fig. 15a

| rank | pathway | p(FDR) |
|---|---|---|
| 1 | Jak-STAT signaling pathway | 5e-09 |
| 2 | Integrin Mediated ECM Sign. | 0.0001 |
| 3 | Axon guidance | 0.0036 |
| 4 | | |
| 5 | Aldosterone-reg. Na reabs. | 0.0190 |
| 6 | Adipocytokine signaling | 0.0326 |
| 7 | | |
| 8 | Nat. killer cell med. cytotox. | 0.0344 |
| 9 | Regulation of actin cytosk. | 0.1403 |
| 10 | Compl. and coag. cascades | 0.3413 |
| 11 | Adherens junction | 0.3413 |
| 12 | SNARE interac. in ves. trans. | 0.4842 |
| 13 | Circadian rhythm -mammal | 0.5074 |
| 14 | Lysosome | 0.6552 |
| 15 | Protein proc. in endoplasmic ret. | 0.7182 |
| 16 | Vibrio cholerae infection | 0.7182 |
| 17 | ***Focal adhesion | 0.9844 |
| 18 | Type I diabetes mellitus | 1 |
| 19 | Phagosome | 1 |
| 20 | Huntington's disease | 1 |
| | Cell cycle | 1 |

Fig. 15b

|  | Y | $P_1$ | $P_2$ | $P_3$ | ... | $P_k$ |
|---|---|---|---|---|---|---|
| $g_1$ | 1 | 0 | 1 | 1 | : | 0 |
| $g_2$ | 1 | 0 | 1 | 0 | : | 0 |
| $g_3$ | 1 | 1 | 0 | 0 | : | 1 |
| : | : | : | : | : | : | : |
| $g_{n-1}$ | 1 | 0 | 0 | 1 | : | 0 |
| $g_n$ | 1 | 0 | 1 | 0 | : | 0 |
| $g_{n+1}$ | 0 | 0 | 0 | 1 | : | 0 |
| $g_{n+2}$ | 0 | 1 | 0 | 1 | : | 0 |
| : | : | : | : | : | : | : |
| $g_{n+m-1}$ | 0 | 1 | 0 | 0 | : | 0 |
| $g_{n+m}$ | 0 | 0 | 0 | 0 | : | 0 |

GENETIC, METABOLIC AND BIOCHEMICAL PATHWAY ANALYSIS SYSTEM AND METHODS

CROSS-REFERENCE TO RELATED APPLICATIONS

This application claims the benefit of U.S. Provisional Application No. 61/735,732, filed on Dec. 11, 2012. The entire disclosure of the above application is incorporated herein by reference.

GOVERNMENT RIGHTS

This invention was made with government support under R01 DK089167 awarded by National Institutes of Health. The government has certain rights in the invention.

FIELD

The present disclosure relates generally to gene, metabolic, biochemical and other pathway analysis. More particularly the disclosure relates to computer-implemented bioinformatic techniques for analysis and for correction of crosstalk effects in pathway analysis.

BACKGROUND

U.S. Pat. No. 8,068,994 describes a method of performing impact analysis of genes (or proteins or metabolites or reactants) that are different between different phenotypes Without limitation, such phenotypes can be disease tissue vs. healthy tissue, treated with a drug vs. untreated, treated with drug A vs. treated with drug B, different time points in a time series measuring changes after a given intervention, etc. Without loss of generality, we will henceforth refer to the illustrative example of a phenotype comparison between disease and healthy.

The biological pathway(s) impacted in a disease state are predicted by (a) providing expression level data for a plurality of biomolecules differentially expressed in the disease state, compared with same biomolecules expressed in the healthy state; (b) determining the significance of the changes in the levels of the biomolecules in disease state; (c) determining the effect(s) of each biomolecule from the plurality of biomolecules on the expression of different downstream biomolecules within each pathway to provide a perturbation factor for each biomolecule in the pathway; (d) combining statistical significance of differentially expressed biomolecules present in the disease state, with a sum of perturbation factors for all of the biomolecules, generating an impact factor for each pathway; (e) calculating statistical significance of the observed impact factor based upon determined probability of having statistical significant presence of differentially expressed biomolecules in step (b) and the sum of perturbation factors in step (c); and (f) outputting statistical significance of the involvement of the pathway(s) in the given phenotype.

While the techniques disclosed in U.S. Pat. No. 8,068, 994, work well, We have discovered that when conducting pathway analysis it is important to identify the interactions between different pathways that are significantly impacted in a given condition. None of the existing techniques are able to accomplish this. Currently available approaches calculate a p-value that aims to quantify the significance of the involvement of each pathway in the given phenotype. These p-values have traditionally been thought to be independent. We have discovered however, as the remainder of this disclosure will explain, that pathways can affect each other's p-values through a phenomena we call "crosstalk." This disclosure also describes the first method able to: i) detect the presence of such crosstalk, ii) quantify its extent and iii) assess the impact on a pathway after removing this crosstalk effect.

SUMMARY

This section provides a general summary of the disclosure, and is not a comprehensive disclosure of its full scope or all of its features.

In one aspect, the disclosed computer-implemented system and method i) detect cross-talk phenomena, ii) quantify the amounts of such crosstalk and iii) correct for it. The disclosed method and system for crosstalk analysis involve several steps that may be performed separately or combined.

First, a crosstalk matrix is computed, taking into account an analysis of pairwise crosstalk interactions between pathways in a given condition. The matrix is useful, for example, in producing a heat map visualization showing the p-value of each pathway when the effect of genes from each other pathway are removed. Through this visualization the extent of crosstalk effects can be better analyzed.

Second, sub-pathways are identified through a module detection step that identifies sub-pathways that appear to be involved in the specific condition studied. This allows a sub-pathway to be studied independently of the pathway to which they belong.

Third, maximum impact estimation is performed, where the biological impact of each gene is assigned to only one of the pathways to which the gene belongs.

The second and third steps collectively create a new set of pathways that are not affected by crosstalk effects.

In a fourth step, new p-values can be computed for each pathway, building a ranked list from which false positives due to crosstalk have been removed.

Computation of the crosstalk matrix may be performed using a computer to construct an impact matrix whereby each gene contributes to one and only one pathway. The computer is then used to process the impact matrix by applying a likelihood-based estimation upon the impact matrix and thereby identify a new set of pathways that is not affected by crosstalk effects.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1a and 1b illustrate the results of ORA analysis in a fat remodeling experiment for the comparison between day 3 and day 0. FIG. 1a shows the results before correction for crosstalk effects; FIG. 1b shows the results after correction for crosstalk effects. All p-values have been FDR-corrected.

Figures 4A, 4B:
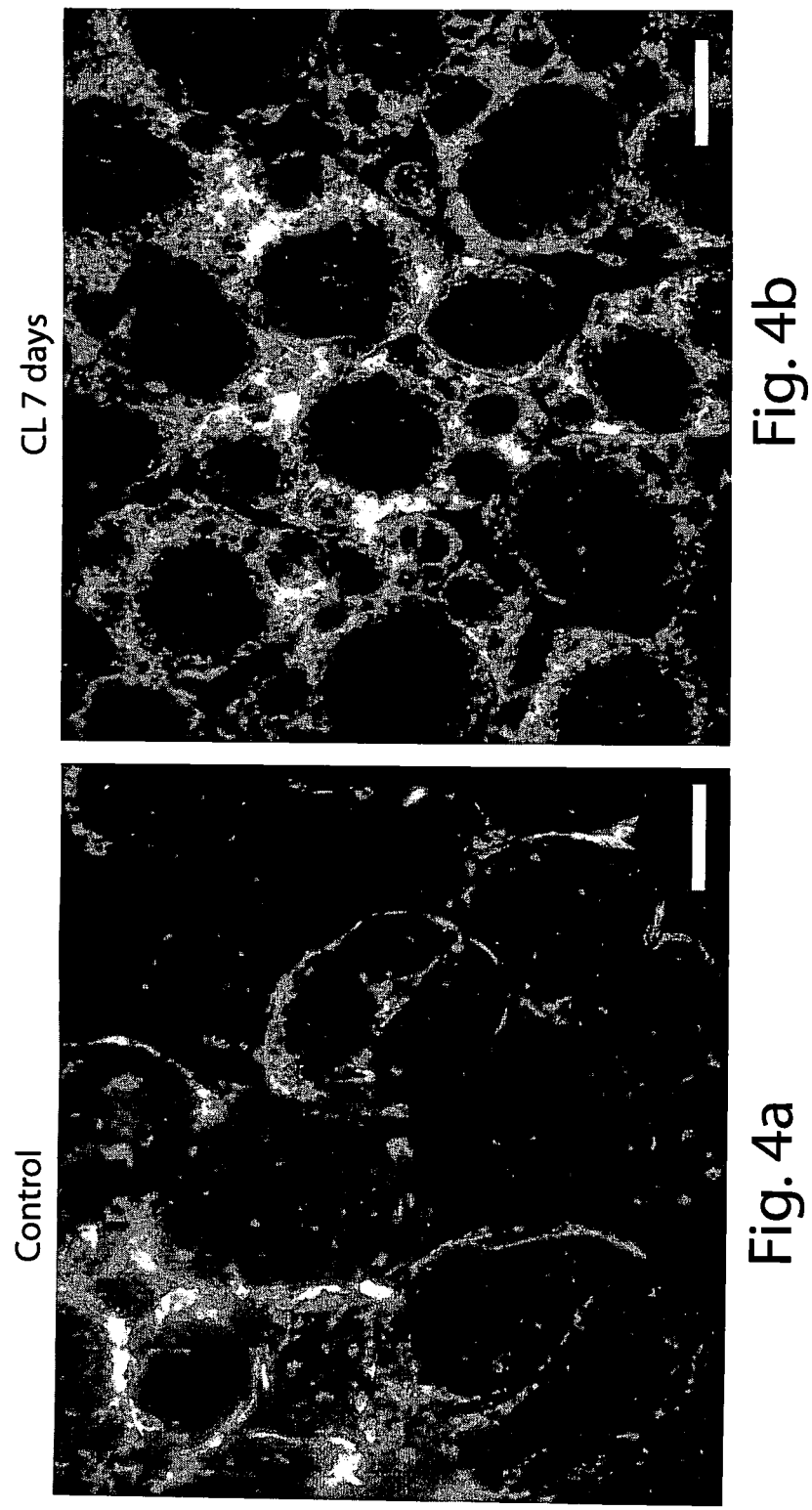

FIGS. 4a and 4b are photomicrograph images of ependymal white adipose tissue of a control mouse; FIG. 4a of a control mouse and FIG. 4b of a mouse treated with CL for 7 days, showing that the treatment triggered massive mitochondrial biogenesis, demonstrating in vivo that indeed, the mitochondrial pathway is central in this experiment. The white bar scale in both figures represents a 20 micron length.

FIGS. 5a and 5b illustrate the ORA results for the cervical ripening experiment, FIG. 5a showing before and FIG. 5b showing after the correction for crosstalk effects. All p-values are FDR-corrected.

Figure 6:
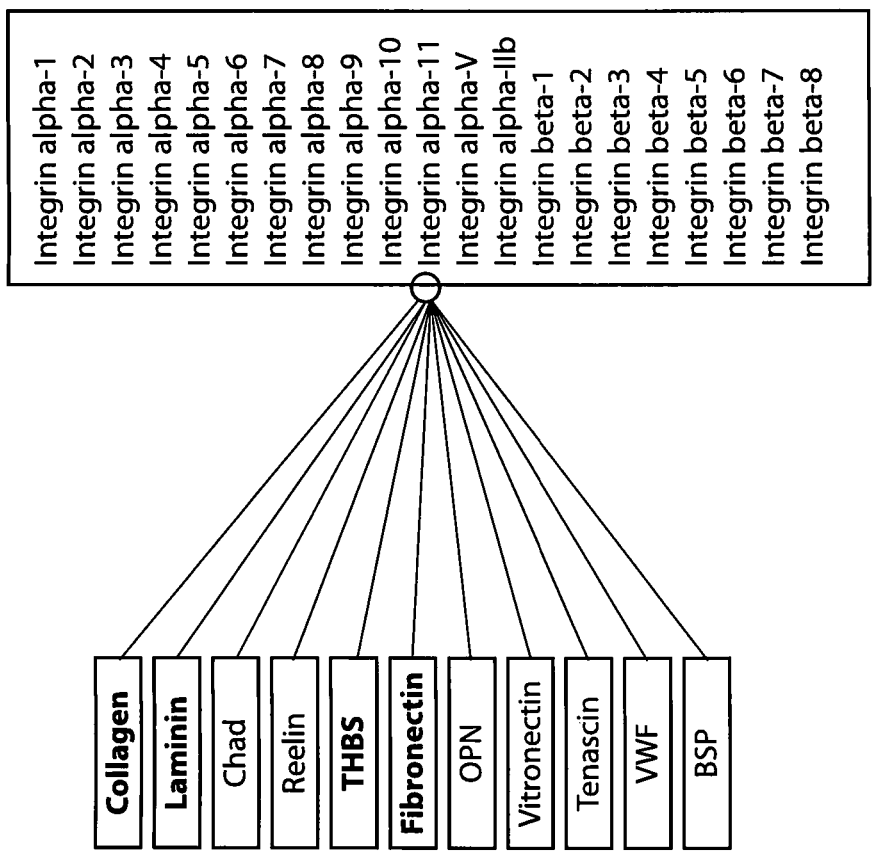

FIG. 6 depicts the novel Integrin-Mediated ECM Signaling. This new module was found to be independently activated and statistically significant in two different conditions: hormone treatment of post-menopausal women and cervical ripening in normal pregnancies. Genes shown in Bold were found to be differentially expressed in the hormone treatment experiment.

FIGS. 7a and 7b are tables comparing the classical over-representation analysis (FIG. 7a) with the crosstalk matrix analysis proposed here (FIG. 7b).

Figure 8:
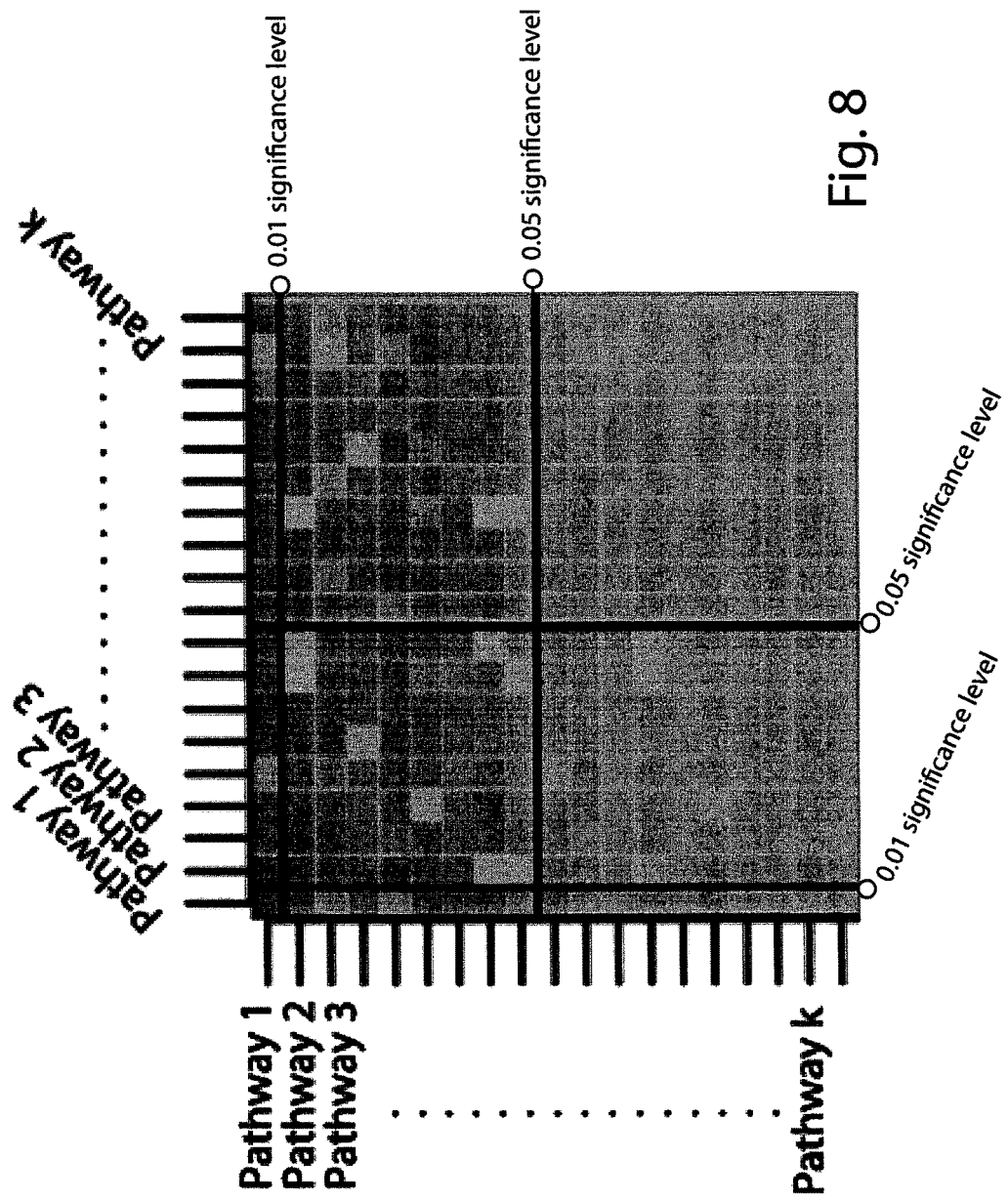

FIG. 8 is an exemplary crosstalk matrix. The p-values in the matrix have been log-transformed (base 10 log) and the sign of the result has been inverted.

Figure 9:
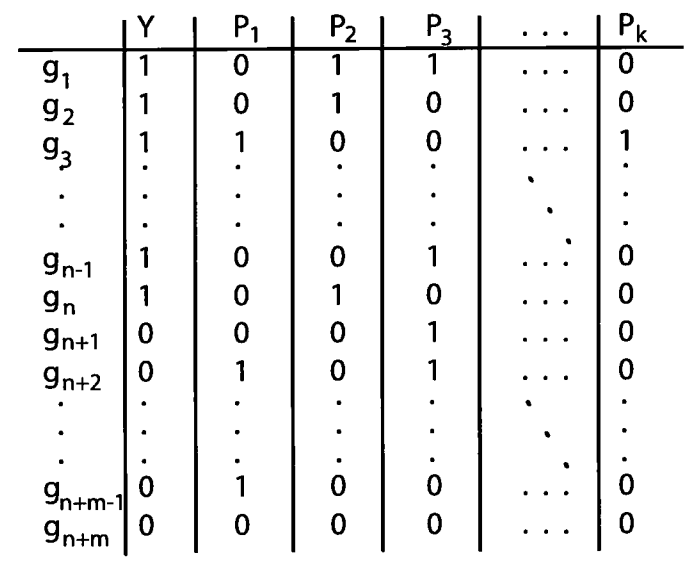

FIG. 9 is an example of a DE/membership matrix. The column Y represents the indicator of differential expression of the various genes (1 for the nDE genes and 0 for the m NDE genes). Column $P_j$ represents the membership indicator for pathway j. Row $g_i$ describes genes i in terms of its differential expression and its membership to the various pathways.

Figure 10C:
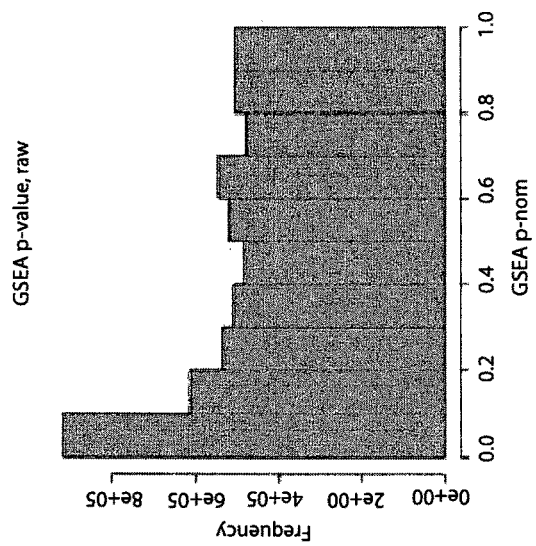
Figure 10B:
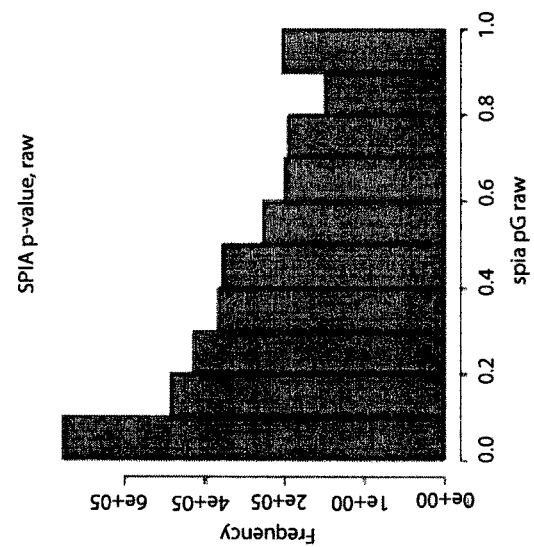
Figure 10A:
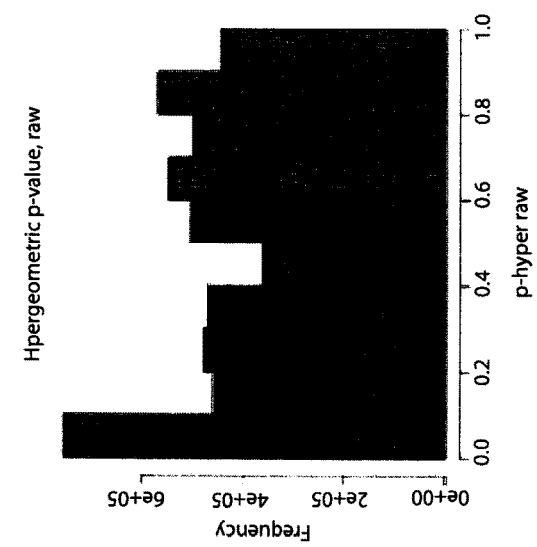

FIGS. 10a, 10b and 10c (collectively FIG. 10) are graphs depicting the distributions of p-values obtained from three different analysis methods under the null hyptothesis: hypergeometric (left), SPIA (middle) and GSEA (right). All three exhibit a significant departure from the expected uniform distribution (Kolmogorov-Smirnov p-values of the order of $10^{-16}$ in all cases). Notably all methods yield a much higher than expected number of pathways with p-values lower than 0.1, i.e. false positives.

Figure 11:
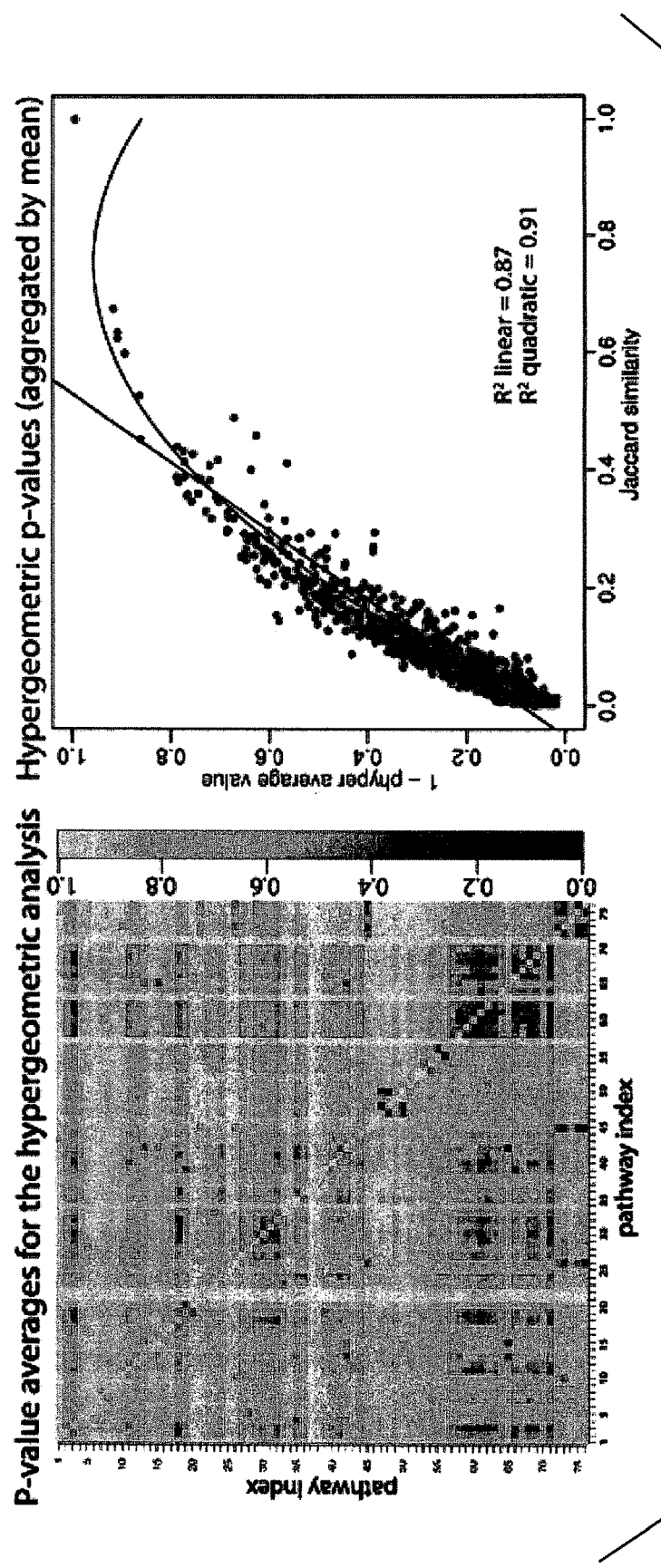

FIG. 11 are graphs showing pathway coupling in the hpergeometric analysis. The left panel shows a number of random genes were chosen from a "bait" pathway i such that its hypergeometric p-value is 0.01. Other genes were chosen randomly from all other pathways (acting as preys), up to a constant number (n=100). The elements [i, j] where i=6 j represent the mean of the distribution of p-values for 1000 random trials using pathway i as bait and pathway j as prey. The elements [i, i] (on the diagonal) represent the classical hypergeometric p-value of pathway i. The data show that a considerable number of pathways influence each other through a "coupling" of the p-values. For instance, row 3 of the matrix shows that when pathway 3 is chosen to be significant, several other pathways (e.g. columns 57 to 70) also tend to be significant (dark shades of blue represent significant p-values). Right panel: each point represents the average of the p-values of all the random trials for pairs with the same Jaccard index. The lines represent the fitting of linear and a quadratic models. Both models show a strong dependence between the p-value coupling and the Jaccard index. Similar results were obtained for GSEA and impact analysis (see FIG. 12).

Figure 12:
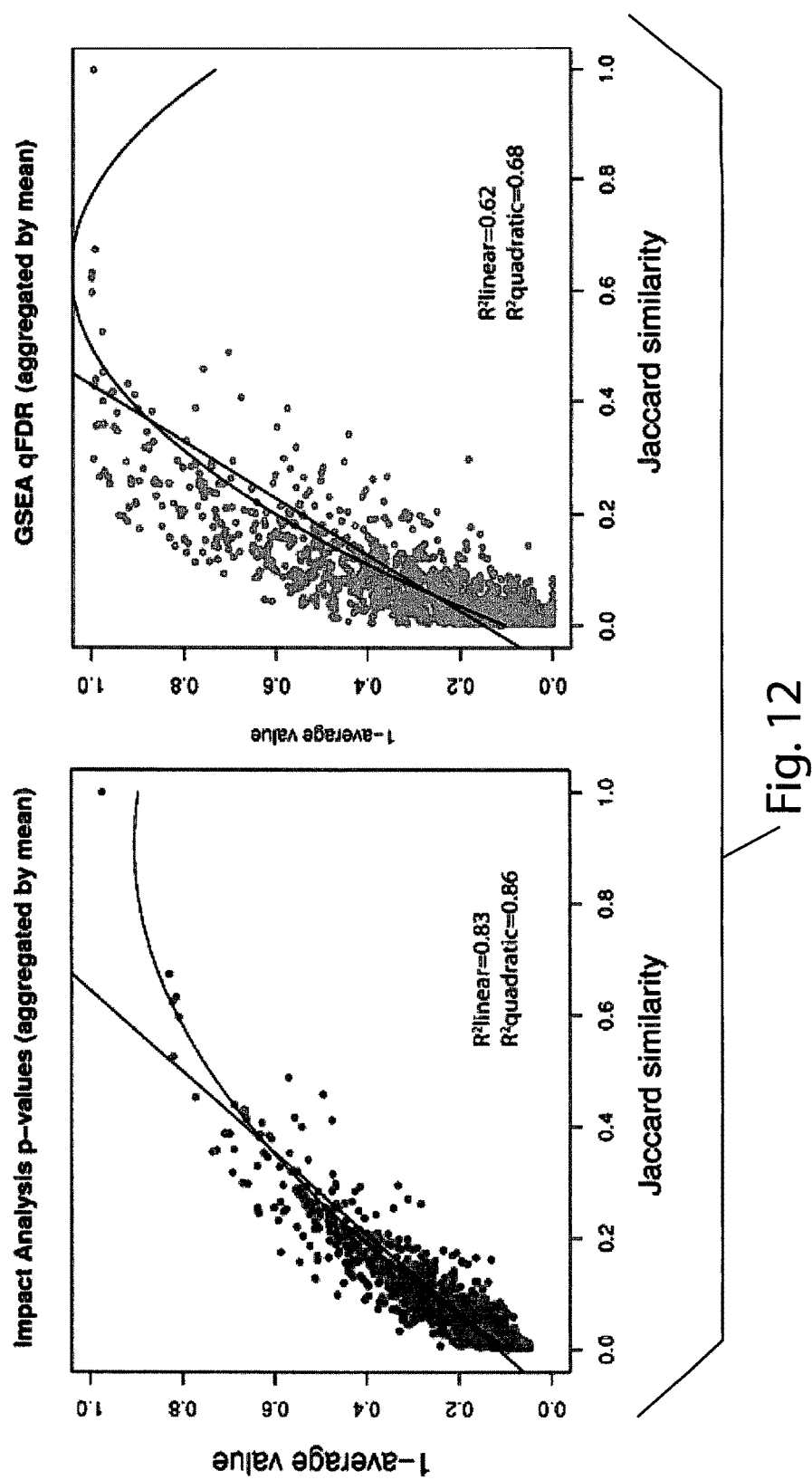

FIG. 12 are graphs showing the pathway coupling in the impact analysis (left panel) and GSEA (right panel). Each point represents the mean of all p-values of all random trials for pairs with the same Jaccard Index. The lines represent the fitting of linear and quadratic models. Both models show a strong dependence between the p-value coupling and the Jaccard Index.

Figure 13:
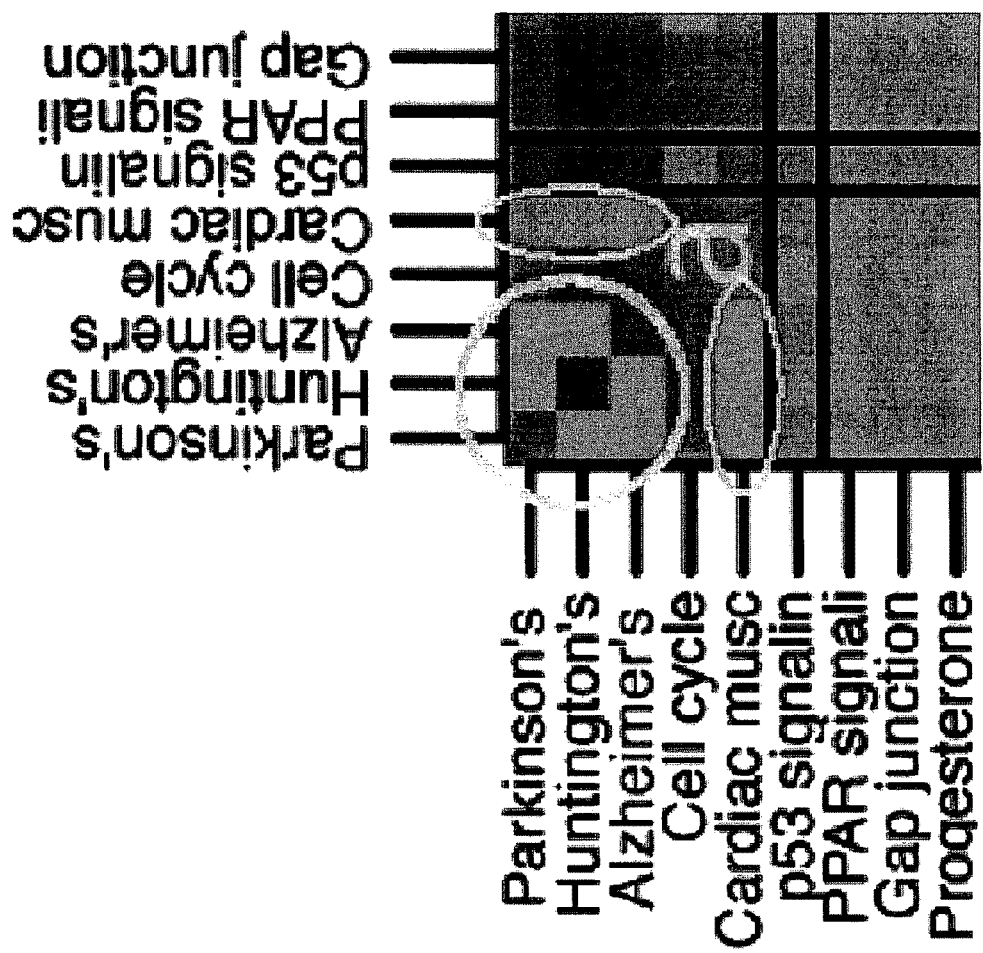

FIG. 13 is a detail of the crosstalk matrix for the comparison between days 7 and 0 in the same treatment. The areas marked with a correspond to the Mitochondrial activity pathway shown in FIG. 3, the same pathway that was found to be activated in the dataset associated with the comparison of expression levels at days 3 and 0.

FIGS. 14a and 14b show tabular results of the ORA for the fat remodeling experiment for the comparison between day 7 and day 0, with results "before" shown on the left (FIG. 14a) and "after" shown on the right (FIG. 14b). All p-values are FDR corrected. As depicted, in the "before" case on the left, the top 20 pathways resulting from classical ORA before correction for crosstalk. Four out of the top five pathways are not related to the fat remodeling phenomenon (false positives). As depicted in the "after" case on the right, the top 20 pathways after the correction for crosstalk effects. The mitochondrial activity pathway (validated in vivo) is reported as the most significant pathway even after 7 days, suggesting permanent tissue remodeling. The Phagosome pathway, significantly impacted after 3 days (see FIG. 1b) is not significant anymore after 7 days, consistent with the transitory nature of cellular death and phagocytosis. The four false positives in the left table have been removed. The ARVC is reported as a false positive but the DE genes located on this pathway are involved in cell adhesion which may be relevant here.

FIGS. 15a and 15b are tables depicting the results of ORA for the estrogen treatment experiment, before (left) and after (right) the correction for crosstalk effects. All p-values are FDR corrected. As illustrated in the "before" case (left), the top 20 pathways reported by the classical ORA before correction for crosstalk. The NSCLC, known to be linked to this treatment[15] is not identified by the classical method, while the SCLC, which showed no increase in incidence in the treatment group,[15] appears as significant. The significance of Pathways in Cancer is consistent with the putative link between hormone treatments and higher incidence of some types of cancer but offers no explanation or insight into the underlying mechanisms. As illustrated in the "after" case (right) the top 20 pathways reported by ORA after the correction for crosstalk effects. The correction method removed Pathways in Cancer, SCLC, and Prostate Cancer from the list of significant pathways, increasing the significance of pathways offering more insights such as Jak-STAT signaling pathway and the new Integrin mediated ECM signaling module. A star before the name of the pathway means that a module overlapping with other pathways has been removed from the pathway.

Figure 16:
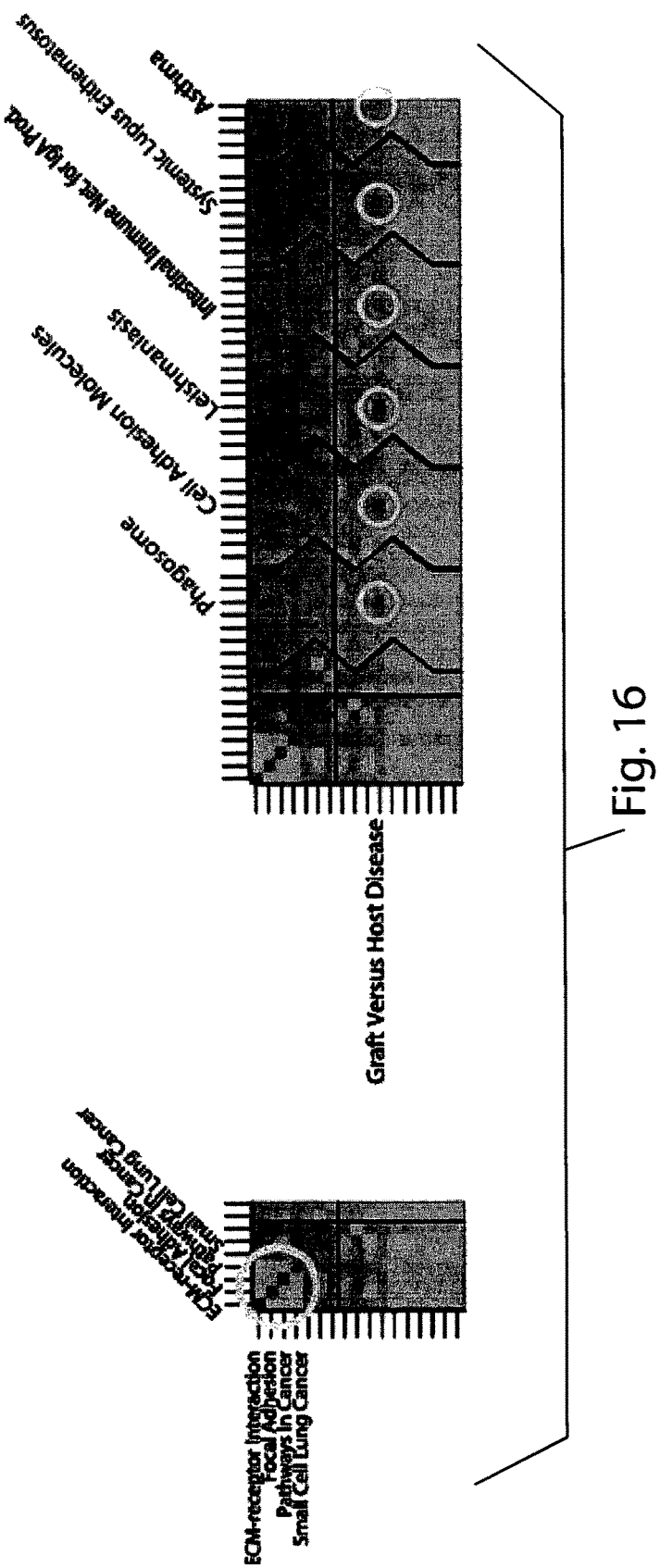

FIG. 16 provides a detail of the crosstalk matrix of the estrogen treatment. Left panel: the circle highlights an example of a common module that is responsible for the significance of an entire group of pathways. The common module between the pathways ECM-Receptor Interaction, Focal Adhesion, Pathways In Cancer, and Small Cell Lung Cancer describes the interaction between integrin and collagen, laminin, and fibronectin. Henceforth, we will refer to this module as the Integrin-mediated ECM signaling pathway (see FIG. 6). Right panel: row corresponding to the pathway Graft-Versus-Host disease. The pathway becomes significant after the removal of specific pathways, highlighted by the yellow circles. The set of pathways includes Phagosome, Cell adhesion molecules (CAMs), Leishmaniasis, Intestinal immune network for IgA production, Systemic Lupus Erithematosus, and Asthma. This indicates a situation in which the genes specific to Graft-Versus-Host disease are related to the phenomenon in analysis, but their significance is masked by the presence of crosstalk with other pathways.

Figure 17:
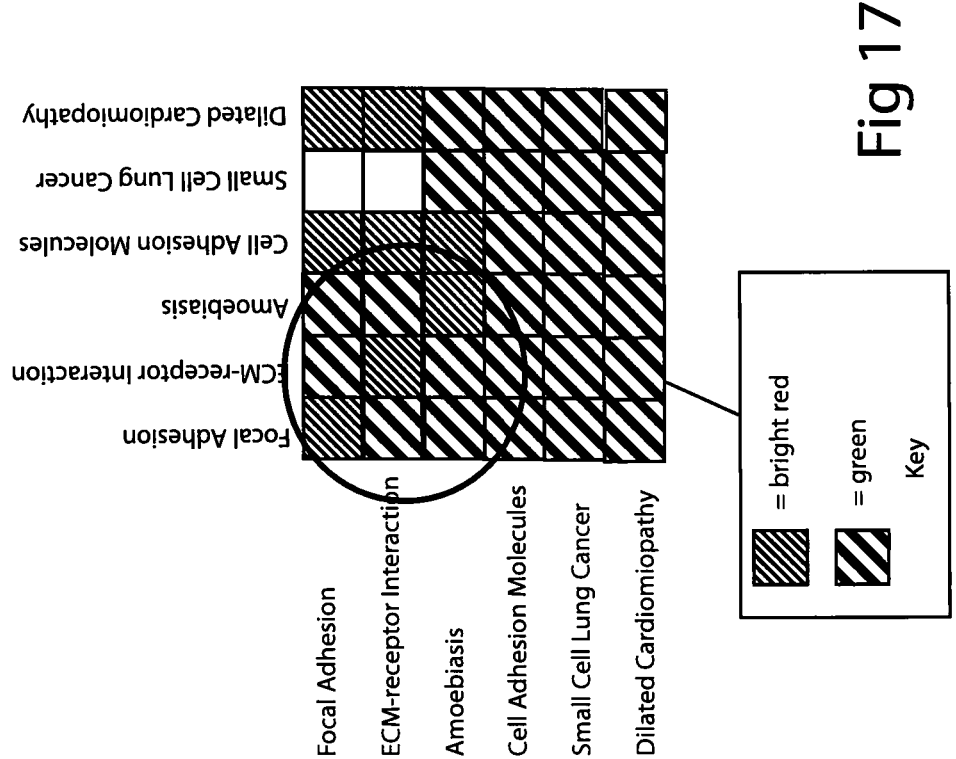

FIG. 17 provides details of the crosstalk matrix of the cervical ripening experiment. The circle highlights the evidence for an independent module involving pathways Focal Adhesion, ECM-Receptor Interaction, and Amoebiasis. This module is exactly the Integrin-mediated ECM signaling previously identified in the hormone treatment experiment (FIG. 6) from a different set of crosstalk interactions. The bright green loss of significance of Small-Cell Lung Cancer in columns 1-3, shows that this pathway was a false positive in the ORA since its significance was due only to the crosstalk from the first 3 pathways.

FIG. 18 is a table which provides an example of a DE/membership matrix; the column Y represents the indicator of differential expression of the various genes (1 for the n DE genes and 0 for the m NDE). Column Pj represents the membership indicator for pathway j. Row gi describes gene i in terms of its differential expression and its membership to the various pathways.

Figure 19:
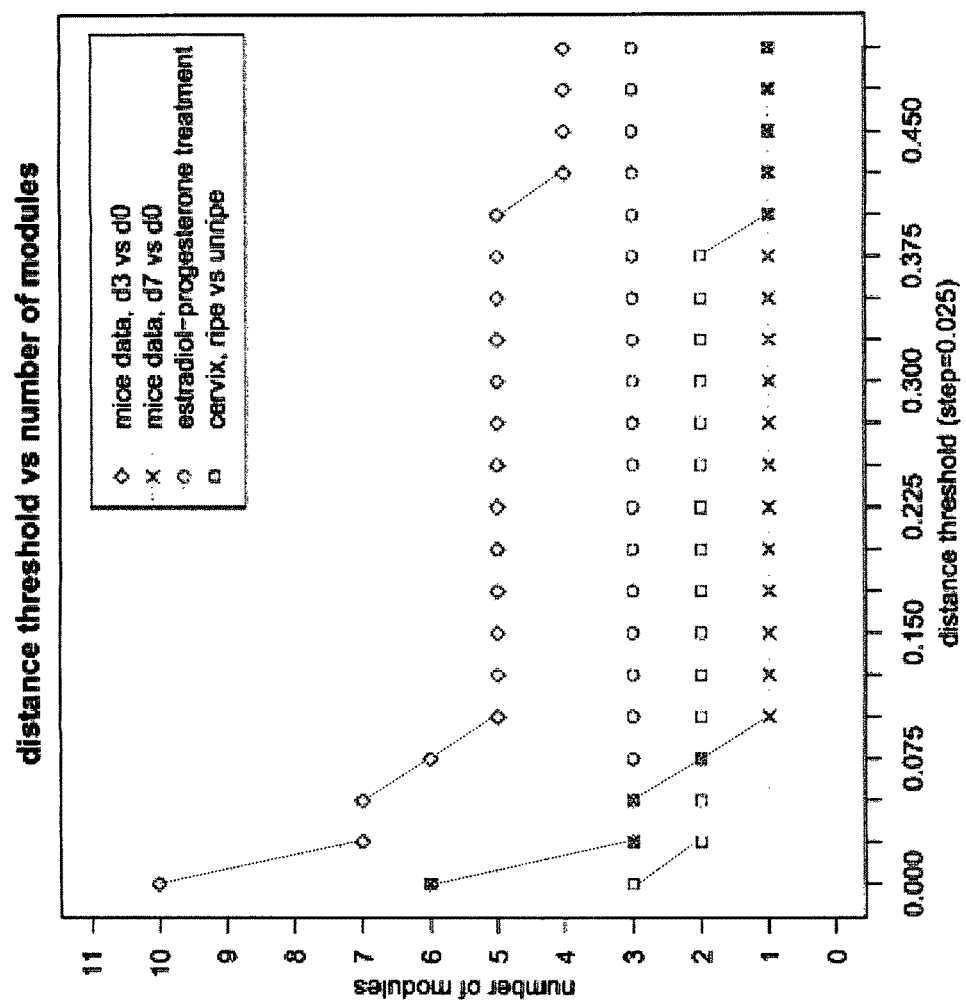

FIG. 19 is a graph depicting the number of modules obtained when changing the threshold distance under which two modules are considered similar enough to be joined. All data sets showed a plateau in the [0.1, 0.375] range indicating that the number of modules found does not depend on the choice of the threshold for a wide range of threshold values.

Corresponding reference numerals indicate corresponding parts throughout the several views of the drawings.

DETAILED DESCRIPTION

Example embodiments will now be described more fully with reference to the accompanying drawings.

Identifying pathways that are significantly impacted in a given condition is a crucial step in the understanding of the underlying biological phenomena. All approaches currently available for this purpose calculate a p-value that aims to quantify the significance of the involvement of each pathway in the given phenotype. These p-values were previously thought to be independent. Here, we show that this is not the case, and that pathways can affect each other's p-values through a "crosstalk" phenomenon that affects all major categories of existing methods. We describe a novel technique able to detect, quantify, and correct crosstalk effects, as well as identify novel independent functional modules. We assessed this technique on data from four real experiments coming from three phenotypes involving two species.

The correct identification of the signaling and metabolic pathways involved in a given phenotype is a crucial step in the interpretation of high-throughput genomic experiments. Most approaches currently available for this purpose treat the pathways as independent. In fact, pathways can affect each other's p-values through a phenomenon we refer to as crosstalk. Although it is intuitive that various pathways could influence each other, especially when they share genes, the presence and extent of this phenomenon have not been rigorously studied and, most importantly, there is no currently available technique able to quantify the amount of such crosstalk. There are three major categories of methods that aim to identify significant pathways: enrichment analysis (e.g. hypergeometric), functional scoring (e.g. GSEA), and topology-based methods (e.g. impact analysis). Here we show that the results of all these methods are affected by crosstalk effects, and that this phenomenon is related to the structure of the pathways. We propose the first approach that can: i) detect crosstalk when it exists, ii) quantify its magnitude, iii) correct for it, resulting in a more meaningful ranking among pathways in a specific biological condition, and iv) identify novel functional modules that can play an independent role and have different functions than the pathway they are currently located on. This method is expected to allow a better understanding of individual experiment results, as well as a more refined definition of the existing signaling pathways for specific phenotypes.

Crosstalk Effects

In order to demonstrate the existence and assess the extent of crosstalk effects, we conducted a systematic exploration of this phenomenon. We constructed a reference set of genes from all genes present in at least one KEGG signaling pathway (2,963 genes at the time). Then, each pathway was used as a "bait", choosing from it a number of genes that would make it significant at a chosen significance level ($\alpha=0.01$ after Bonferroni correction). Other random genes were selected up to a constant number (n=100) of "differentially expressed" (DE) genes (details discussed below). Under these circumstances, the research hypothesis is true for the bait, while the null hypothesis is true for all other pathways. We repeated this selection 1,000 times for each pathway Pi, and each time we computed the hypergeometric,[1] SPIA (impact analysis), and GSEA p-values for all pathways from the KEGG database.[7] With these results, we constructed the empirical distributions of the False Discovery Rate (FDR)-corrected p-values corresponding to each prey Pj. The distributions of the p-values for all three methods are severely skewed towards zero, showing that all methods produce a significant number of false positives due to crosstalk effects (FIG. 10). We hypothesized that crosstalk is mostly due to the common gene between pathways. If this were true, we would expect to see a strong coupling between pairs of pathways with many genes in common and a weak coupling between pathways that do not share any genes. In order to test this hypothesis, we calculated the Jaccard similarity index for each pair of pathways, as well as the Pearson correlation between the Jaccard index and the p-values of the preys (FIGS. 11 and 12). The data shows a very strong correlation (Pearson correlation index of 0.87 for hypergeometric, 0.62 for GSEA and 0.83 for SPIA), which confirms our hypothesis that the crosstalk can be explained by the presence of "busy" genes, i.e. genes that are involved in more than one pathway.

Results

Crosstalk Analysis and Correction.

The method we propose for correcting for crosstalk effects takes as input a set of reference pathways and a list of genes that are DE in the given condition. The crosstalk analysis is composed of three steps. The first step is the computation of a crosstalk matrix, i.e. the analysis of pairwise crosstalk interactions between pathways in the given condition, resulting in a heat map showing the p-value of each pathway when the genes from each other pathway are removed. This matrix allows the visualization of various cases of crosstalk effects and provides information on the extent of crosstalk effects in the condition analyzed. The second step is the module detection that allows the identification of sub-pathways that appear to be involved in the specific condition studied independently of the pathway they belong to. The final step is the maximum impact estimation, where the biological impact of each gene is assigned to only one of the pathways to which the gene belongs, for those genes that belong to more than one pathway. The result of the last two steps is essentially a new set of pathways that can include: a) original pathways as found in the literature, b) novel functional modules that might be relevant to the given condition, and c) pathways modified by the removal of a such a functional module. The new set of pathways is not affected by crosstalk effects, and new p-values are computed for each pathway, building a ranked list from which the false positives due to crosstalk have been removed (see Materials and Methods below).

Fat Remodeling in Mice.

We include here the results of the crosstalk analysis in an experiment investigating cellular and metabolic plasticity of white fat tissue (WAT), where the classical overrepresentation analysis (ORA) produced a number of false positives, and failed to rank highly pathways that were known to be involved in the given condition. In this experiment, the chronic activation of WAT β-adrenergic receptors by certain physiological and pharmacological conditions transforms the tissue into one resembling brown fat, a thermogenic organ. The data set was obtained from a microarray analysis of white fat from mice treated with low dose (0.75 nmol/hr) CL 316,243 (CL) for 0, 3 and 7 days. Here we discuss only the list of DE genes coming from the comparison between expression levels of genes at days 3 and 0 (for the comparison between days 7 and 0, see discussion below).

The top 20 pathways ranked by ORA and their associated FDR-corrected p-values are shown in FIG. 1a. The three most significant pathways in the comparison between days 3 and 0 were Parkinson's, Alzheimer's and Huntington's diseases. The fourth pathway in the ranked list is Leishmaniasis. The first three pathways describe degenerative diseases of the central nervous system which have no connection to fat remodeling. Leishmaniasis describes the signaling involved in a disease spread by the bite of certain species of sand flies. Clearly, this pathway is also unlikely to give insights about the fat remodeling phenomenon. While other pathways such as Phagosome, PPAR Signaling, and Cell cycle, are definitely more related to the phenomenon of fat remodeling, their presence in the middle of a ranked list dominated by false positives (6 false positives in the 10 pathways significant at 1%) illustrates how the crosstalk effects make the classical ORA unable to find the truly relevant pathways.

Figure 2:
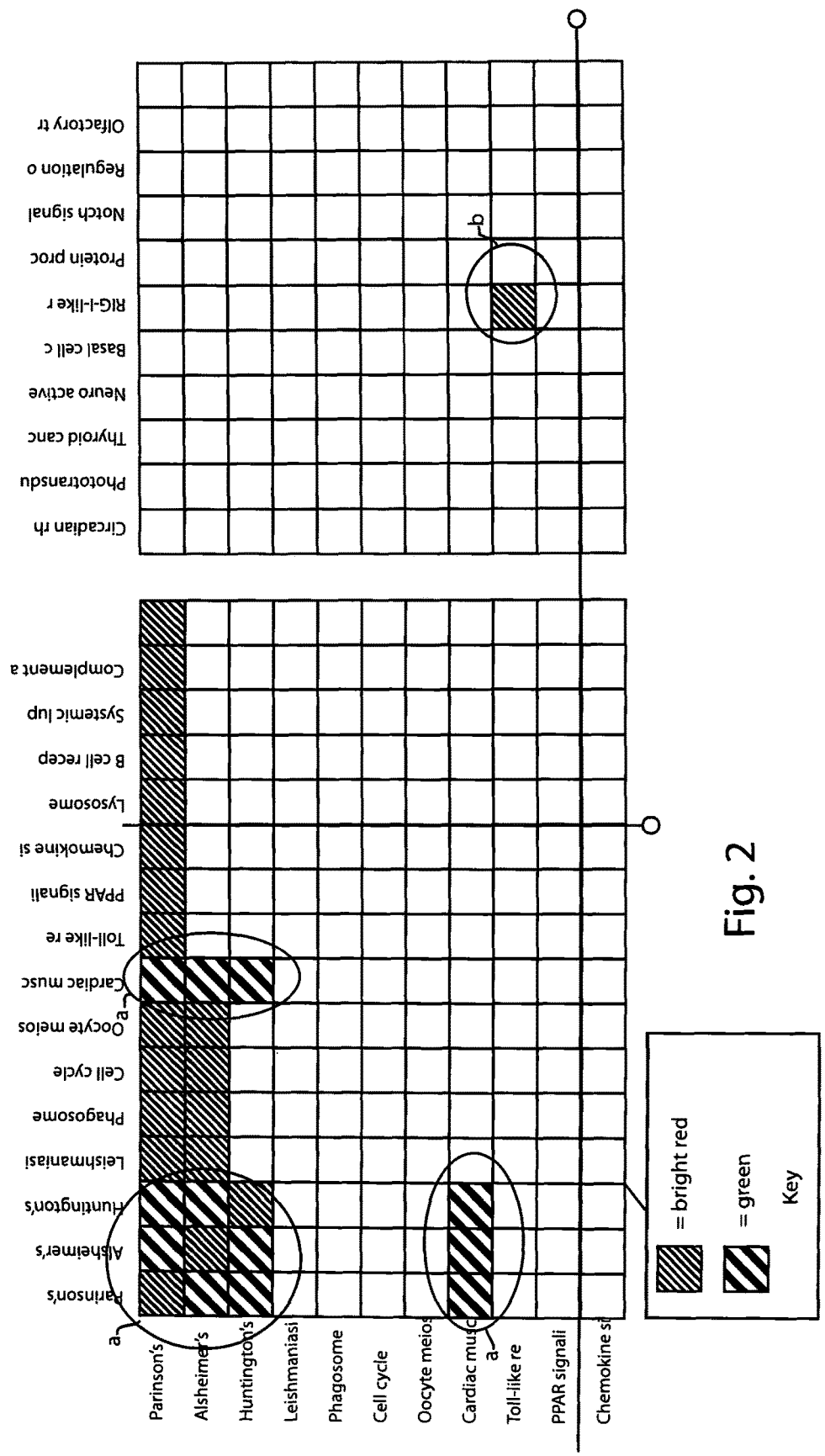
FIG. 2 is a crosstalk matrix "heat map" diagram comparing day 3 and day 0 in the CL treatment.

In order to analyze and eliminate the crosstalk effects we computed the crosstalk matrix as described in the Methods section. The analysis of the matrix illustrates some interesting examples of crosstalk effects. FIG. 2 represents a detail of the entire matrix. If desired the matrix may be generated using different colors to depict different significance levels. In the exemplary illustration of FIG. 2 crosshatched patterns have been used instead of colors, to support a black & white representation for Patent Office convenience. Some "colors" have been suppressed in FIG. 2 to simplify the explanation. In this figure, the high significance of Parkinson's (bright red in row 1, column 1—see Key for color designators) disappears when the crosstalk due to Alzheimer's is eliminated (green in row 1, column 2—see Key for color designators). This indicates that Parkinson's is a false positive, since its significance is due exclusively to genes from Alzheimer's. Furthermore, the high significance of Alzheimer's (bright red in row 2, column 2) also disappears when the crosstalk effect of Parkinson's is eliminated (green in row 2, column 1). This means that Alzheimer's significance is also due only to the genes in common with Parkinson's. Essentially, the analysis tells us that the genes in common between the two pathways are activated independently of either pathway, which suggests that these genes constitute an independent functional module. The same phenomenon involves the Cardiac Muscle Contraction and Huntington's disease pathways. The same independent functional module is responsible for the changes shown in areas marked with a in FIG. 2.

Figure 3:
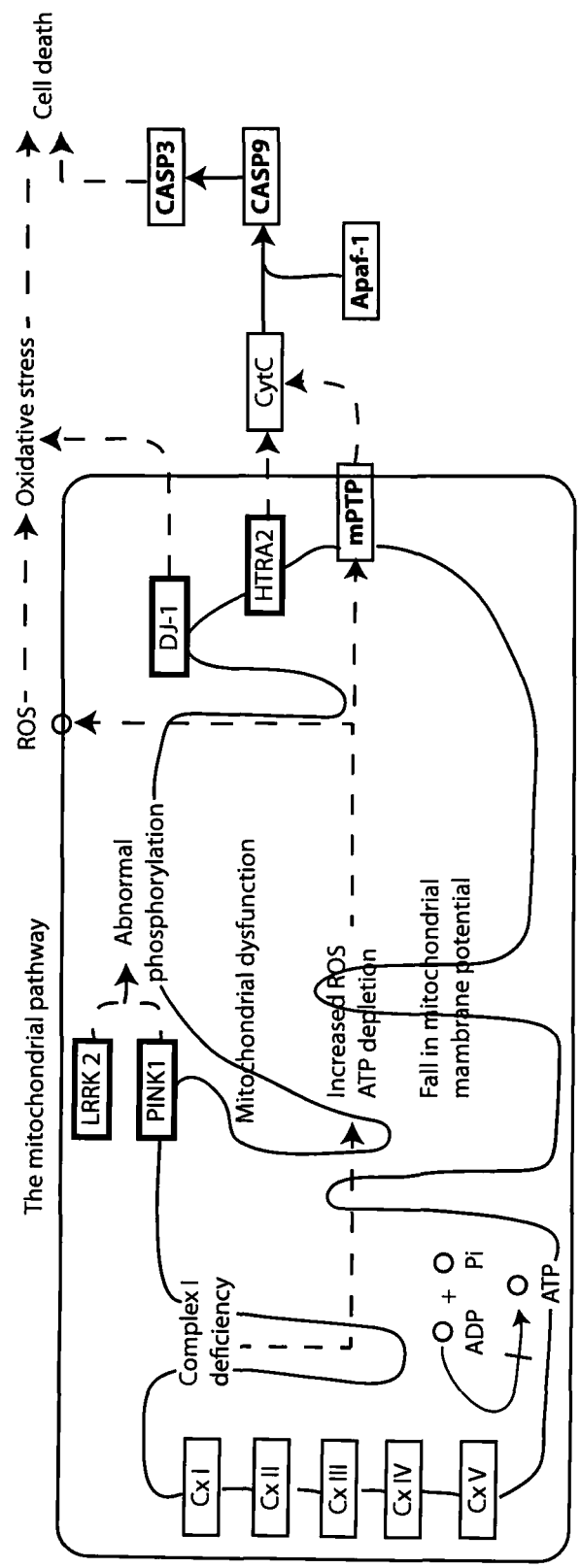
FIG. 3 illustrates the mitochondrial activity pathway, an independent functional module responsible for incorrect identification of the pathways Parkinson's disease, Alzheimer's disease, Huntington's disease and Cardiac Muscle Contraction by classical ORA.

An inspection of these genes and their signaling mechanisms reveals that this module is composed by genes present in mitochondria, organelles involved in all pathways above. The fact that this module is strongly activated in this fat remodeling experiment that is not related to any of the above conditions (Alzheimer's, Parkinson's, Huntington's), suggests that this should be considered as an independent pathway, dedicated to mitochondrial activity. FIG. 3 shows a representation of this new pathway.

FIG. 4 shows a comparison between the control (left) and CL-treated mice (right). The right panel of this figure shows a massive generation of new mitochondria after 7 days of treatment, demonstrating in vivo that indeed, the mitochondrial pathway is central in this experiment.

Another very interesting phenomenon can be observed in FIG. 2 (circle b). Here, Toll-like Receptor Signaling (TLR) pathway becomes more significant when the Rig-I Like Receptor Signaling (RLR) pathway (not significant on its own) is removed. The TLR pathway is the generic pathway involved in the immune response. The RLR pathway is the antiviral innate immunity pathway, which includes the mechanisms specifically aimed at the detection of exogenous DNA or RNA. In essence, the crosstalk analysis tells us that in the fat remodeling experiment, the immune system has been activated but this immune response is not due to the presence of foreign genetic material. This is exactly what happens here. The CL treatment causes the death of some white fat cells. In turn, this causes an immune response in which macrophages are required to dispose of the dead cells. Such subtle distinctions between various triggers that activated the immune response are not possible with any classical analysis methods, and it is remarkable that a data analysis method was able to provide this type of insight.

We then applied the proposed Maximum Impact Estimation described in the Methods section to the data. The corrected p-values are shown in FIG. 1b. The ranking based on these crosstalk corrected p-values is greatly improved. The most significant pathway is now the newly discovered mitochondrial pathway shown in FIG. 3 and validated by the in-situ hybridization shown in FIG. 4. The new p-values also indicate the Phagosome pathway as one of the pathways related to this phenomenon. Third in the list is an independent module shared by Cell Cycle and Oocyte Meiosis. This can be thought of as a pathway related to the creation of new cells. Finally, the true involvement of PPAR signaling pathway in the phenomenon of fat remodeling has been previously demonstrated. After removing the influence of the mitochondrial crosstalk, the Parkinson's, Alzheimer's, and Huntington's pathways are not significant anymore (now ranked $60^{th}$, $61^{st}$ and $54^{th}$, respectively, data not shown). Also, after removing the crosstalk from Phagosome, Leishmaniasis is not significant anymore (now ranked $62^{nd}$, data not shown).

Cervical Ripening.

The second dataset analyzed was obtained from a recent study that investigated the transcriptome of uterine cervical ripening inhuman pregnancy before the onset of labor at term. The tissue analyzed is the human uterine cervix, the lower part of the uterus extending from the isthmus of the uterus into the vagina. It is mainly composed of smooth muscle and extracellular matrix, which consists of collagen, elastin, proteoglycans, and glycoproteins. The uterine cervix has an essential function in the maintenance of pregnancy and also in parturition. Cervical ripening is a critical component of the common terminal pathway of parturition, which includes the extensive remodeling of the cervix. Disorders of cervical ripening can lead to premature or protracted cervical change, complicating term (e.g. protracted dilatation or arrest of dilatation) or preterm gestations (e.g. premature cervical dilation in the second trimester).

The state of cervical ripening has traditionally been assessed by clinical examination (Bishop score or its modifications), which includes the digital examination of the cervix for its consistency, dilatation, effacement, and position. This method has also been used to predict the likelihood that a patient would go into spontaneous labor. The goal of this experiment was to examine the relationship between human cervical ripening and the cervical transcriptome, aiming to improve our understanding of the biology of cervical ripening at term. This study included pregnant women who underwent elective C-section at term with an unripe (n=11) or ripe cervix (n=11). Cervical biopsies were obtained from these women transvaginally, from the anterior lip of the uterine cervix following C-section. Microarray analysis was performed on RNA isolated from these cervical tissue specimens using Affymetrix GeneChip HGU133Plus2.0 arrays.

On the same dataset we performed the comparison between gene expression levels from cervical tissues obtained from women with an unripe (n=11) or ripe cervix (n=11) using the classical ORA. The results are shown in FIG. 5a. Pathways with a p-value smaller than 0.05 after FDR correction were Focal adhesion, ECM-receptor interaction, Amoebiasis, Cell adhesion molecules (CAMs), Small cell lung cancer, and Dilated cardiomyopathy.

There is plenty of experimental evidence that biological processes described by the pathways Focal Adhesion, ECM-Receptor Interaction, and Cell Adhesion Molecules are related to cervical ripening. The relation between these pathways and the phenomenon in analysis was revealed by studies on humans and animals showing the involvement of extra-cellular matrix metabolism and cell adhesion molecules in cervical ripening. However, the pathway Amoebiasis describes the biological process of infection from a parasite that invades the intestinal epithelium. Amoeba infection involves the parasite attachment to the intestinal mucus layer, followed by disruption and death of host epithelial cells. This process is completely unrelated to the physiological condition of cervical ripening in term pregnancy. The same is true for the Small Cell Lung Cancer pathway. Clearly, the top ranked pathways include some describing complex phenomena that are unrelated to the studied condition. Also, the significant pathways known to be involved in the process of cervical ripening are somewhat general pathways describing cellular interactions.

The analysis of the crosstalk matrix (see FIG. 17) shows that there is an independent functional module among the top three pathways in the ranking. This novel module includes the genes present in the interaction between the cellular transmembrane protein integrin and three important ECM components, collagen, laminin, and fibronectin. The KEGG pathways involved in the identification of this pathway are Focal adhesion, ECM-receptor interaction, and Amoebiasis. Henceforth, we will refer to this pathway as the Integrin-Mediated ECM Signaling (FIG. 6).

Very interestingly, the independent functional module found in this condition is, in fact, the exact same module found in the hormone treatment experiment described below. Interestingly, the KEGG pathways involved in the identification of this functional module are slightly different between the two phenotypes. While in this phenotype this module was found from the interaction of Focal adhesion, ECM-receptor interaction and Amoebiasis, in the hormone treatment the last pathway is replaced by Pathways in Cancer. The fact that the same module was found to be activated and statistically significant in two different phenotypes, from the interaction of different sets of canonical pathways, further supports the idea that this module describes an independent mechanism and should therefore be considered as an independent pathway.

Further analysis of the crosstalk matrix shows that the Small Cell Lung Cancer loses significance when the crosstalk effects of the first three pathways are removed (bright green loss of significance in first 3 columns of row 5 in FIG. 17). This allows us to conclude that it is a false positive in the classical ORA, with its ORA significance due exclusively to crosstalk effects.

The ranking of pathways after applying our analysis is shown in FIG. 5b. The first pathway is Integrin-mediated ECM Signaling with an FDR corrected p-value of $2.9e^{-13}$. Cell Adhesion Molecules is now the second in ranking, with an FDR corrected p-value of 0.004. The false positives in the classical ORA results, Amoebiasis and Small Cell Lung Cancer, are not significant anymore. The biological significance of the pathway Dilated Cardiomyopathy may be linked to the fact that 10° lo-15° lo of the uterine cervix is constituted of smooth muscle, and cervical ripening involves alterations of this component. The last significant pathway at the 5° lo significance threshold is Leukocyte Transendothelial Migration. Although human and animal studies have shown that cervical ripening does not require activation of a typical inflammatory response, and influx of inflammatory cells into the cervix, the significance of this pathway may reflect the beginning of later inflammatory events typical of parturition.

In addition to these data sets, we analyzed another data set coming from the comparison of expression levels at days 7 and 0 in the fat remodeling experiment (see the Supplementary Results section below), as well as a data set investigating the effect of various types of hormones on the endometrium of healthy post-menopausal women who underwent hysterectomy. This approach was able to eliminate most false positives, as well as correctly identify as significant pathways that had been biologically proven to be involved in the given condition, yet not found to be significant by the classical analysis. We also found several independent functional modules including a mitochondrial activity module active in a different stage of fat remodeling, and an integrin-mediated ECM signaling found to be involved in hormone treatment in post-menopausal women and cervical ripening. Interesting, the later module was extracted independently from the crosstalk interactions of two different groups of pathways, in the two conditions analyzed.

Conclusions

These results show that our method for the detection and correction for crosstalk effects allows not only the elimination of most of the false positives present in the results of the classical ORA, but also the identification of novel functional sub-pathways that are specifically involved in the condition studied, giving useful insights on the phenomenon in analysis that are not captured by existing techniques. This is a departure from the current paradigm that considers the pathways as static models, independent of the phenotype. In the view proposed here, various specific modules, or sub-pathways, can be dynamically linked to specific conditions.

When such independent functional modules are identified in independent conditions, such as the integrin-mediated ECM signaling above, these modules could be considered as candidate new pathways.

Online Methods

Pathway Analysis in the Presence of Overlapping Pathways: The Crosstalk Matrix.

Our goal is to develop an approach that can detect and quantify the crosstalk between pathways. The main issue we are trying to address here is the fact that in the presence of overlapping pathways (i.e. for all pathways databases available today) crosstalk phenomena increase the probability of false positives, i.e. increase the number of pathways reported as significant but that in reality are not interesting (borrowing terminology from Brad Efron, we call pathways that have lesser biological significance "not interesting" even though they might be statistically significant with a large enough sample size).

To better understand the approach we are going to present, let us briefly review the classical hypergeometric approach described above. FIG. 7a represents the contingency table used for assessing the significance of a pathway $P_i$ by the classical ORA approach. The table divides genes as either being in the pathway or not, versus being considered DE or not DE (NDE); $n_i$ represents the number of DE genes on $P_i$, while n represents the total number of DE genes, and $m_i$ represents the number of NDE genes on $P_z$ while m represents the total number of NDE genes. It follows that $n_i+m_i=|P_i|$ represents the number of genes on $P_i$, while with n+m we represent the total number of genes.

The reasoning behind the over-representation (ORA) analysis is that if the number of DE genes on a pathway is much higher than expected by chance, then the pathway is likely to be biologically interesting. In order to take into account the effect of the overlap on the significance of the two pathways we consider the effect of the removal of the overlapping part on the significance of the pathways. This is achieved as follows: let us consider two overlapping pathways $P_i$ and $P_j$. With the notation $P_{i\setminus j}$ we define the set of elements in $P_i$ excluding the intersection with $P_j$; in the same way, with the notations $n_{i\setminus j}+m_{i\setminus j}$ we represent the number of genes that are in pathway $P_i$ but not in pathway $P_j$, and with $n_{i\setminus j}$ the number of DE genes that are on pathway $P_i$ but not in pathway $P_j$. We then consider the contingency table shown in FIG. 7b, whose bottom margin is identical to that of FIG. 7a.

With this contingency table, we compute for every pair of pathways [i,j] the p-value of $P_{i\setminus j}$. Since this computation yields an k×k matrix, where k is the number of pathways, the results are most conveniently represented using a heat map of the negative log p-values. Each cell (i,j) of this matrix characterizes the significance of pathway $P_i$ when we remove the effect of pathway $P_j$. The rows and the columns are ordered by the original p-values of the pathways, which are placed on the diagonal. We will refer to this matrix as the crosstalk matrix. This matrix is useful for identifying the effects of crosstalk among pathways.

An example of the crosstalk matrix can be found in FIG. 8. We will refer to the part of the matrix above the horizontal significance threshold as the significance strip. The non-significance strip will be the part below the horizontal significance threshold. The significance quadrant will be the part of the significance strip to the left of the significance threshold. Using these terms, we can identify and discuss several interesting phenomena that are not captured by any of the existing pathway analysis methods.

A first interesting case is when a pathway $P_i$ is reported as significant by the classical analysis, but it loses its significance when the effect of another pathway $P_j$ is removed. This is represented, in the crosstalk matrix, by a non-significant p-value (green square) in the significance strip. In this case $P_i$ is unlikely to be biologically meaningful, since its significance is most likely due to a crosstalk from $P_j$.

A second interesting case is when a pathway $P_i$ that is not significant for the classical analysis becomes significant when the crosstalk effect of another pathway $P_j$ is removed. This is represented in the crosstalk matrix by a significant p-value (red square) in the non-significant strip. The meaning of this is that pathway $P_j$ was masking the significance of $P_i$, indicating that a phenomenon likely to be biologically meaningful is happening in the part of $P_i$ which is not in common with $P_j$.

A third and last interesting case is a symmetric (with respect to the diagonal) decrease in significance of pathways in the significance quadrant. This indicates the presence of an independent functional sub-module, common to both $P_i$ and $P_j$, that is responsible for their significance. Note that the activity of this module is tightly related to the condition studied.

The Maximum Impact Estimation: An Expectation Maximization Technique for the Assessment of the Significance of Signaling Pathways in Presence of Crosstalk.

The crosstalk matrix is a useful tool for the interpretation of the effect of crosstalk between pathways. However, the ultimate goal of the analysis of signaling pathways is to provide a meaningful ranking among pathways, as well as a p-value quantifying the likelihood that a certain pathway is involved in the phenomenon in analysis. Here, we developed a correction method for the ranking of pathways that takes in account the overlaps between pathways.

The main idea is that, if there is no crosstalk, then there is no ambiguity in the ORA significance calculations. In such a case, if genes in a path are over-represented, it cannot be a false positive caused by crosstalk. Our approach is therefore to infer an underlying pathway impact matrix where each gene contributes to one and only one pathway, hence is devoid of crosstalk, and then to perform the ORA analysis using that impact matrix. Since this underlying pathway impact matrix is not observed directly, it is inferred through likelihood-based methods, and estimated using the EM algorithm. The corrected ranking is computed using ORA analysis with the underlying pathway impact matrix, shown as follows.

Let us consider the DE indicator vector Y, representing the differential expression of genes, and the membership matrix X describing the membership of each gene in each one of k pathways $P_1 \ldots P_k$. The vector Y is defined as follows:

$$Y_i = \begin{cases} 1 & \text{if } g_i \text{ is } DE \\ 0 & \text{if } g_i \text{ is } NDE \end{cases}$$

and each cell $X_{i,j}$ of the matrix X is defined as follows:

$$X_{ij} = \begin{cases} 1 & \text{if } g_i \text{ belongs to } P_j \\ 0 & \text{if } g_i \text{ does not belong to } P_j \end{cases}$$

The matrix Y|X obtained by combining the vector Y with the X matrix is shown in the example in FIG. 9.

In many analysis methods, the membership matrix X is also interpreted as the impact matrix: if $X_{ij}=1$, then gene g impacts pathway $P_j$. In ORA, for example, each gene is considered to have the same full impact on all pathways the gene belongs to. Crosstalk effects result from the fact that a gene can belong to more than one pathway, but in principle, it can potentially have a different biological impact on each such pathway. Our aim is to identify the pathway where the biological impact of such a shared gene is maximum. We do so by estimating the maximum impact pathway using an expectation maximization approach (see discussion below).

Identification of Independent Functional Modules.

The maximum impact estimation procedure alone is not be able to identify overlapping modules responsible for the entire significance of other pathways, as in the situations represented by case 3 in the section describing the crosstalk matrix. In such cases the overlap should be considered as a separate pathway that is more likely to be biologically meaningful in the condition under analysis. An additional step is needed in order to correctly deal with this situation. In this additional step, we extract certain significant overlaps from the list of pathways, and include them in the list as independent functional modules. An independent functional module is a module for which there is evidence of an activity independent of the pathways it resides in, for the given condition. If an independent module is found in more than one, possibly unrelated, conditions, this module is considered as a candidate novel pathway.

A module must satisfy certain conditions in order to be treated as an independent functional module. Let us assume that we are analyzing the overlap between the pathways $P_i$ and $P_j$; the first condition is that both pathways are significant (after correction for multiple comparisons) at a certain threshold $\alpha$. This condition limits the search to the significance quadrant of the crosstalk matrix. The second condition is that the overlap $P_{i \cap j}$ itself must be significant at $\alpha$. The third condition is that the sub-pathways obtained by removing the overlap from both original pathways, indicated by $P_{i \setminus j}$ and $P_{j \setminus i}$ must not be significant at $\alpha$. If we denote with p(P) the p-value of a generic pathway P, then the conditions can be summarized as follows:

$$p(P_i) < \alpha, p(P_j) < \alpha \quad\quad 1$$

$$p(P_{i \cap j}) < \alpha \quad\quad 2$$

$$p(P_{i \setminus j}) \geq \alpha, p(P_{j \setminus i}) \geq \alpha$$

This pairwise procedure might yield modules that are similar one to each other, for example in cases where a module is contained in three or more pathways. That could be solved with a three-way or n-way search, but we opted for another approach for limiting the number of new modules. Once all interesting pairwise modules are created, we test for similarity among modules. The index used for similarity is a modified Jaccard Similarity index mJS defined as follows:

$$mJS = \frac{|M_1 \cap M_2|}{\min(|M_1|, |M_2|)} \quad\quad (1)$$

where $M_1$ and $M_2$ are two modules obtained with the search criteria explained above. We merge any two modules similarity is greater that a certain threshold st. Once the modules are merged, the similarity among all the modules (including the newly created one) is computed again, and the merging procedure is applied again until there are no more modules that can be merged.

This newly created modules are removed from all pathways with which they overlap, and this list of modified pathways is used in the EM procedure. For the data sets analyzed in this work, we used a threshold of 0.25. The motivation for the selection of this threshold is discussed below.

After applying the module discovery and the EM approach, the result is a modified membership matrix that can be used to perform the desired type of analysis. This matrix now includes three types of pathways: i) original pathways as found in the literature, ii) novel functional modules that are impacted in the given condition independently from the pathways they belong to, and iii) the pathways from which such independent modules have been removed. If the same independent module is found in several conditions, in other words if this module is active independently from its parent pathways in several different phenotypes, such a module should be considered a good candidate for a novel pathway.

Crosstalk Phenomena

We hypothesized that pathways can consistently affect each other's p-values in significant ways through crosstalk. Identifying such effects in any number of specific real experiments would constitute only anecdotal evidence since the true amount of crosstalk between two given pathways in any given condition is not known. In order to demonstrate the existence and assess the extent of crosstalk effects, we designed and conducted the following systematic exploration of this phenomenon. We first constructed a reference set of genes from the union of all genes present on at least one KEGG signaling pathway (2963 genes at the time). Then, for each pathway $P_i$, we ran experiments as follows. We first calculated the number $n_i$ of DE genes that would make $P_i$ significant at least at $\alpha=0.01$ after a Bonferroni correction for multiple comparison. Henceforth, we will refer to this pathway as the "bait". We then used the reference set to pick $n_i$ random genes from $P_i$ and $100-n_i$ genes that are not on $P_i$, and calculated the hypergeometric significance of all other "prey" pathways, $P_j$. This essentially models a situation in which 100 genes are found to be DE, and these genes are such that the hypergeometric analysis will find the bait pathway $P_i$ significant at 1% after the correction for multiple comparisons. Since the $100-n_i$ genes that are not on $P_i$ are randomly chosen among the reference set, no other pathway $P_j$ should have more genes than expected by chance. Under these circumstances, the research hypothesis is true for the bait, while the null hypothesis is true for all other pathways. We repeated this selection 1,000 times for each pathway $P_i$, and each time we computed the hypergeometric, SPIA (impact analysis), and GSEA p-values for all pathways in the set S including all the pathways from KEGG. With these results, we constructed the distributions of the FDR-corrected p-values corresponding to each prey $P_j$. Under the null hypothesis, the p-values are expected to follow an uniform distribution, and to be independent between different pathways. In fact, the distributions of the p-values (see FIGS. 10a, 10b and 10c) are significantly different from the uniform distribution (Kolmogorov-Smirnov goodness of fit p-values of the order of $10^{-16}$ in all cases). The distributions for all three methods are severely skewed towards zero, showing that all methods produce a large number of false positives.

Furthermore, we observed much stronger crosstalk effects for specific pathway pairs (i,j): every time one of them is used as a bait, the p-value of the other one is pulled to values much lower than expected by chance, many times well below the significance threshold. All crosstalk effects can be represented in a crosstalk matrix (left panel in FIG. 11). In this matrix, the elements [i, j] represent the mean of the distribution of p-values for 1,000 random trials using pathway i as bait and pathway j as prey. This matrix is not symmetrical since the influence of pathway i on pathway j can be different from the influence of pathway j on i. The matrix shows strong crosstalk between several pathways (e.g. row 3 and columns 57 through 70).

We hypothesized that this crosstalk is due mostly to the genes that are in common between pathways. If this were true, we would expect to see a strong coupling between pairs of pathways that have many genes in common and a weak coupling between pathways that do not share any genes. In order to test this hypothesis, we calculated the Jaccard similarity index between all pairs of signaling pathways from KEGG. The Jaccard index is defined as $$\frac{|P_i \cap P_j|}{|P_i \cup P_j|}$$

and characterizes the overlap between two sets, relatively to the size of their union. Pathways that share many genes will have a large Jaccard index. The right panel in FIG. 11 shows the relationship between the hypergeometric p-values and the Jaccard index for all pathway pairs. The data shows a very strong correlation between the two (Pearson correlation index of 0.87), which confirms our hypothesis that the crosstalk can be explained by the presence of "busy" genes, i.e. genes that are involved in more than one pathway. Very similar results have been obtained for FCS analysis (GSEA) and for the impact analysis (SPIA) (see FIG. 12). The Pearson correlation between the p-values provided by GSEA and the Jaccard indices of all KEGG pathways was 0.62, while in the case of SPIA the correlation was 0.83.

Supplementary Results

Fat Remodeling in Mice.

The first additional results to be discussed here were obtained from the comparison between expression levels of genes at days 7 and 0 in the same fat remodeling experiment discussed in the main article. The genes were ordered by p-values and the top 5% were selected as differentially expressed (DE). The results of the classical ORA are shown in FIG. 14a (only the top 20 pathways are shown). The top pathways are Parkinson's disease, Alzheimer's disease, and Huntington's disease, diseases that have little to do with the tissue remodeling phenomenon. The Cell Cycle pathway is likely to be related to tissue remodeling, and p53 Signaling is known to be a central pathway in the response to cellular stress, including inflammation, and related to processes like cellular senescence and cell cycle. With four false positives in the top five pathways, the results of the classical ORA are distorted by pathway crosstalk phenomena to the point of being useless.

In order to identify and eliminate the crosstalk effects we computed the crosstalk matrix described in the Materials and Methods section. FIG. 13 represents a detail of the entire matrix.

The areas marked with a highlight the same phenomenon present in the matrix corresponding to the comparison between days 3 and 0 of the same experiment. The significance of the pathways Parkinson's disease, Huntington's disease, Alzheimer's disease, and Cardiac Muscle Contraction is entirely due to the same mitochondrial activity pathway shown in FIG. 3 in the main text. The greatly enhanced mitochondrial activity in the treated tissue was validated in vivo by in-situ hybridization (see FIG. 4 in the main text). This shows additional evidence towards the activation of this independent pathway in this condition.

We then applied the proposed Maximum Impact Estimation (fully described in Materials and Methods) to the data set. The ranking obtained with the p-values corrected for crosstalk is shown in FIG. 14b and is greatly improved. The most significant pathway is the mitochondrial pathway, showing that greatly enhanced mitochondria activity continues to be the most important difference between the treated and untreated cells even after 7 days. This in turn suggests that the tissue underwent along-lasting remodeling phenomenon, in addition to a number of transitory phenomena such as cellular death and phagocytosis (note that the Phagosome pathway, significantly impacted after 3 days is not significant anymore after 7 days). The pathway ranked second is Arrhythmogenic Right Ventricular Cardiomiopathy. While this pathway was treated here as a false positive due to lack of literature evidence linking it specifically to tissue remodeling, the module reported by the method includes genes related to desmosomes, cell structures responsible for certain types of cellular adhesion which may also be relevant here. Fourth and fifth pathways in rank are, respectively, the PPAR Signaling pathway and the Cell Adhesion Molecules pathway, both closely related to the phenomenon of fat remodeling.

Estrogen Treatment on Post-Menopausal Women.

The second data set we include here was produced by an experiment investigating the effect of various types of hormones on the endometrium of healthy, post-menopausal women who underwent hysterectomy. Hormone therapy has been used for the treatment of conditions associated with menopause. Estrogen replacement therapy has been proven useful against the insurgence of collateral effects of the post-menopausal syndrome. However, the administration of estrogens only has been shown to increase the incidence of endometrial carcinoma. Therefore, in addition to estrogen, progestins are now given to menopausal women. Although the risk of endometrial cancer is reduced with the addition of progestins, the incidence of other forms of cancer seems to increase when progestin is administered with estrogen. Initiatives like the Million Women Study and the Women Health Initiative showed that hormone replacement therapy can increase the risk of lung and breast cancer. In this context, it is interesting to compare the effects of various combinations of hormones at the transcriptome level.

Here, we illustrate our analysis method on the comparison of the expression levels of genes from samples treated with estrogen (E2) plus medroxyprogesterone acetate (MPA) versus normal samples. The classical over-representation analysis (ORA) finds the following pathways significant at the 5% level after FDR correction: ECM receptor interaction, Focal Adhesion, Pathways in Cancer, Small Cell Lung Cancer, Axon Guidance, Prostate Cancer, and Jak-STAT Signaling. These results are shown in FIG. 15a.

The E2+MPA is known to be associated with certain type of cancer including non-small-cell lung cancer (NSCLC). Hence, the presence of Pathways in Cancer is justified, even though its identification as significant does not help understand the specific mechanism that might be active here. However, the set of significant pathways include small-cell lung cancer (SCLC) which is not known to be associated with this treatment and fail to include the NSCLC which has been linked to it. Prostate Cancer is also unlikely to be related to this specific treatment given that this treatment is administered to women, rather than men. Like in the previous case, the presence of false positives and the presence of pathways describing general cellular adhesion processes (focal adhesion and ECM-receptor interaction) does not help with the understanding of the underlying phenomenon.

After applying our analysis method to the dataset, the results are more helpful in providing insights about the specific underlying mechanisms, as shown in FIG. 15b. The first pathway in the ranked list is the Jak-STAT signaling pathways. Indeed, there is evidence that estrogen treatments impact such pathway through interaction with the suppressor of cytokine signaling (SOCS). The second pathway is a new pathway, based on the module common between Focal Adhesion, ECM-receptor Interaction, and Pathways in Cancer (see the left panel of FIG. 16). In this figure, within the significant quadrant, the symmetric pattern that can be observed between the three pathways above and Pathways in Cancer indicate the presence of a functional module that responds specifically to the hormone treatment. Interestingly, this pathway is the same pathway that has been shown to be active in a completely different phenotype, the cervical ripening experiment described in the main text, the Integrin-Mediated ECM Signaling described in FIG. 6. This pathway is responsible for the significance of the top four pathways in FIG. 15a.

As in the experiment studying cervical ripening, this novel pathway is composed of genes present in the interaction between the cellular transmembrane protein integrin and three important ECM components, collagen, laminin, and fibronectin, all of which appeared as differentially expressed in hormone treatment compared to the control. This is interesting because the ECM-receptor interaction carries two major functions: the first is to transduce extracellular signals into the cell for regulation of downstream pathways possibly through focal adhesion complex, and the second function is to provide structural support to resident cells; the binding between integrins and collagen, laminin, fibronectin is involved in the second process. Collagen, a major component of the ECM, forms fibers and attaches to the cell surface through binding with integrins and fibronectins. Collagen is also present in the basement membrane with laminin, forming a thin sheet of fibers that underlies the epithelium. Previous studies have shown that collagen, laminin, and fibronectin participate in regulating normal development of mammalian mammary tissues. They also play an important role in cancer progression possibly through ECM remodeling, which leads to alterations in cell adhesion and tumor cell motility. Consistent with this, enhanced attachment of estrogen-dependent breast cancer cells to the substrate containing ECM components (collagen I and IV, laminin, fibronectin) was observed with E2 treatment. More evidence was provided in recent studies using mouse mammary epithelial cells, where the expression of estrogen receptor α (ERα) was greatly down-regulated by integrin-mediated interaction with collagen-IV and laminin, rather than effects of growth factors such as insulin. Consistently to the previous findings, our method finds that it is the module describing the interaction between integrin and collagen, laminin, and fibronectin (rather than the interaction between ligands and their receptors) that is affected specifically by the hormone treatment, a striking pattern unlikely to be detected by classical over-representation analysis.

A similar pattern was observed between pathways Prostate Cancer and Focal Adhesion, where the removal of a common submodule caused loss of significance in both pathways. A close investigation of the Focal Adhesion pathway revealed that its downstream signaling cascade is regulated by two types of extracellular signals, the ECM components that interact with integrins, and the growth factors (GFs) that bind to the transmembrane GF receptor (GFR). Although a number of DE genes belong to the ECM-Receptor Interaction pathway, it is the GFR-induced signaling cascade that is involved in both Prostate cancer and Focal adhesion, which contains at least two downstream pathways that responded specifically to the E2+MPA treatment. The first one is the canonical Wnt cascade, during which the transcription factor β-catenin gets activated by PI3K-AKT (phosphatidylinositol 3 kinase-V-Akt murine thymoma viral oncogene homolog) mediated signals, and translocate into the nucleus for downstream gene regulation. The other is the classical MAPK (Mitogen-Activated Protein Kinase) pathway, also known as the Raf-MEK-ERK pathway, where Raf (MAPKKK), MEK (MAPKK), and ERK (MAPK) represent the three key serine/threonine-specific protein kinases present in the cascade. What is also noticeable is that in both cases, while Wnt Signaling pathway and MAPK Signaling pathway both contain sub-pathways other than the two highlighted here, such as the Wnt5-induced non-canonical Wnt pathway or JNK-p38-mediated MAPK pathway, only the canonical Wnt cascade and the classical MAPK cascade are associated with both Prostate Cancer and Focal Adhesion, among which a number of important genes are DE under the hormone condition, such as PTEN (phosphatase and tensin homolog), a tumor suppressor that regulates PI3K-AKT signaling pathway, ERK (extracellular-signal-regulated kinase), one of the three key protein kinases in the MAPK pathway, and AR (androgen receptor), an oncogene that plays an important role in MAPK-regulated cell proliferation. Indeed, estradiol has been shown to activate β-catenin-mediated Wnt pathway through inhibition of its partner GSK3 in the rat hippocampus, which releases β-catenin and allows its nuclear translocation. More functional evidence was provided using human colon and breast cancer cells, in which estrogen receptor (ER) and β-catenin were found to participate in the same multi-protein complex, whose interaction gets enhanced with the presence of estrogen. Since both β-catenin and ER function as transcription factors, it is possible that the role of β-catenin in this complex is to recruit additional co-activators and chromatin remodeling factors that interact with ER for downstream transcriptional regulation. Estrogen has been demonstrated to induce cell proliferation through increased phosphorylation of MAPK cascade, with the mechanistic link between estrogen and MAPK signaling lying in a partner of ER, the MNAR (modulator of non-genomic activity of estrogen receptor) protein. MNAR forms a complex with ER and Src family of tyrosine kinases as a scaffold protein, which is enhanced by E2, further induces activation of ERK kinases and affects ER-mediated transcription. Consistent with these studies, our method detected a module shared between Prostate cancer and Focal adhesion, the GFR-induced canonical Wnt and classical MAPK cascade, which is responsible for significance of both pathways.

Another interesting case is shown in the right panel of FIG. 16. Here, the Graft-Versus-Host Disease pathway gains significance when the crosstalk of various other pathways is removed. This happens because all shared genes between Graft-Versus-Host Disease and the others are all non-DE genes in this condition. In other words, the DE genes present in Graft-Versus-Host Disease pathway are specific to the pathway itself. Among those, two particularly interesting ones are PRF1 (perforin 1) and GZMB (granzyme B), both of which play important functional roles in the natural killer (NK) cell-mediated cytolysis. Consistent with this, the Graft-Versus-Host Disease pathway is highlighted as being significantly affected by the E2+MPA treatment in the crosstalk matrix, not due to other interactions but due to genes specific to NK cell-mediated cytotoxicity. It is remarkable that the results of this type of analysis allowed the identification of a module, composed by genes belonging to the Graft-Versus-Host Disease pathway, that is impacted by the hormone treatment, and whose importance was masked by crosstalk effects with other pathways. This module is relevant in the condition studied, and treating it separately would provide a more accurate understanding of the underlying biological phenomenon. However, since the activity of this module was not identified yet in another condition, nor do we have an independent in vivo validation for this phenotype, we are not proposing this as an independent pathway at this time.

Crosstalk Matrix for the Cervical Ripening Experiment.

The crosstalk matrix for the cervical ripening experiment indicates the presence of an independent functional module among the top three pathways in the ranking. The module is the same module found in the hormone treatment experiment, although in this experiment it is found from the interaction of different pathways. A detail of the crosstalk matrix is shown in FIG. 17.

Materials and Methods

The Maximum Impact Estimation: An Expectation Maximization Technique for the Assessment of the Significance of Signaling Pathways in Presence of Crosstalk.

The crosstalk matrix is a useful tool for the interpretation of the effect of crosstalk between pathways. However, the ultimate goal of the analysis of signaling pathways is to provide a meaningful ranking among pathways, as well as a p-value quantifying the likelihood that a certain pathway is involved in the phenomenon in analysis. Here, we developed a correction method for the ranking of pathways that takes into account the overlaps between pathways.

The main idea is that if there is no crosstalk, then there is no ambiguity in the ORA significance calculations. In such a case, if genes in a pathway are over-represented, it cannot be a false positive caused by crosstalk. Our approach is therefore to infer an underlying pathway impact matrix where each gene contributes to one and only one pathway, hence is devoid of crosstalk, and then to perform the ORA using that impact matrix. Since this underlying pathway impact matrix is not observed directly, it is inferred through likelihood-based methods, and estimated using the EM algorithm. The corrected ranking is computed using ORA with the underlying pathway impact matrix, shown as follows.

Let us consider the DE indicator vector Y, representing the differential expression of genes, and the membership matrix X describing the membership of each gene in each one of k pathways $P_1 \ldots P_k$. The vector Y is defined as follows:

$$Y_i = \begin{cases} 1 & \text{if } g_i \text{ is } DE \\ 0 & \text{if } g_i \text{ NDE} \end{cases}$$

and each cell $X_{i,j}$ of the matrix X is defined as follows:

$$X_{ij} = \begin{cases} 1 & \text{if } g_i \text{ belongs to } P_j \\ 0 & \text{if } g_i \text{ does not belongs to } P_j \end{cases}$$

The matrix Y|X obtained by combining the vector Y with the X matrix is shown in the example in FIG. 18.

In many analysis methods, the membership matrix X is also interpreted as the impact matrix: if $X_{ij}=1$, then gene $g_i$ impacts pathway $P_j$. In ORA, for example, each gene is considered to have the same full impact on all pathways the gene belongs to. Crosstalk effects result from the fact that a gene can belong to more than one pathway, but in principle, it can potentially have a different biological impact on each such pathway. Our aim is to identify the pathway where the biological impact of such a shared gene is maximum. We do so by estimating the maximum impact pathway using an expectation maximization approach as described in the following.

Assuming that in a specific biological condition each gene distributes its impact differently to each pathway, we will consider the pathway to which each gene distributes the greatest fraction of its impact. We define a binary matrix Z that indicates, for each gene, the pathway that receives the biggest fraction of that gene's impact. For each gene $g_i$, the corresponding row $Z_i=[Z_{i1}, Z_{i2}, \ldots, Z_{ik}]$, where $Z_{ij} \in \{0, 1\}$, will have $\Sigma_{j=1}^{k} Z_{ij}=1$, i.e., there is only one column in each row that has a non-zero element. This matrix Z is the unknown underlying pathway impact matrix referred to above; our goal is to estimate it.

Let us consider one row $Z_i$ having a one in an unknown column j and zeros elsewhere. Since we don't know j, we compute the probability of each pathway to be the one where gene $g_i$ gives the greatest fraction of its impact. To do this, we assume a non-negative vector of multinomial probabilities $\Pi=\{\pi_1 \ldots \pi_k\}$ with $\Sigma_{j=1}^{k}\pi=1$, defined by $\pi_j=p(Z_{ij}=1|Y_i=1)$. In other words, given a gene $g_i$ that is DE, $\pi_j$ is the probability that $g_i$ gives the greatest fraction of its impact to $P_j$. Similarly, we also define $\Theta=\{\theta_1 \ldots \theta_k\}$, where $\theta_j=p(Z_{ij}=1|Y_i=0)$ for the NDE genes.

Row i of the membership matrix X is denoted by $X_i$; this vector tells us which pathways gene i belongs to. Within the context of the probabilistic model described above, each row $X_i$ can be interpreted as an observation of a gene with a given expression state Y that give the greatest fraction of its impact to one of the pathways to one of the pathway it belongs to. Therefore, for DE genes we have $p(X_i=x_i|Y_i=1,\Pi)=\Pi \cdot x_i'$. We further assume that the hidden matrix Z is consistent with the observed X, i.e., $Z_{ij}$ can be 1 only when $X_{ij}=1$; if $X_{ij}=0$ then we must have $Z_{ij}=0$ (a gene cannot contribute most to a pathway that it does not belong to). With this notation:

$$p(Z_i = z_i \mid X_i = x_i, Y_i = 1, \Pi) = \frac{p(Z_i = z_i, X_i = x_i \mid Y_i = 1, \Pi)}{p(X_i = x_i \mid Y_i = 1, \Pi)} \quad (1)$$

$$= \frac{I(z_i \cdot x_i' = 1) \cdot \Pi \cdot z_i'}{\Pi \cdot x_i'}$$

where $I(\cdot)$ is the indicator function. For example, if $x_i=(11001)$ and $g_i$ is a DE gene, then the conditional distribution of $Z_i$ is given by:

$p(Z_i=(10000)|X_i=x_i,Y_i=1,\Pi)=\pi_1/(\pi_1+\pi_2+\pi_5)$ $p(Z_i=(01000)|X_i=x_i,Y_i=1,\Pi)=\pi_2/(\pi_1+\pi_2+\pi_5)$ $p(Z_i=(00100)|X_i=x_i,Y_i=1,\Pi)=0$ $p(Z_i=(00010)|X_i=x_i,Y_i=1,\Pi)=0$ $p(Z_i=(00001)|X_i=x_i,Y_i=1,\Pi)=\pi_5/(\pi_1+\pi_2+\pi_5)$ \quad (2)

This yields a vector of conditional probabilities $c_i=(c_{i1}, c_{i2}, \ldots, c_{ik})$ for each row $Z_i$ of DE genes, where $c_{ij}=p$ ($Z_{ij}=z_{ij}|X_i=x_i$) as defined above. Once those probabilities are estimated, we can produce a most likely matrix Z by assigning each gene to the pathway with the highest probability of receiving the biggest fraction of the impact of the gene. Specifically, $z_{ij}=1$ when $\max_s\{c_{is}\}=c_{ij}$; $z_{ij}=0$ otherwise.

If there were no crosstalk, each gene would contribute to a single pathway, the matrix X and the matrix Z would be equal, and they would have only one element equal to 1 in each row. In this case, $\pi_j$ could be estimated as the number of DE genes belonging to the pathway divided by the total number of DE genes. The probabilities $\pi$ and $\theta$ could be estimated as follows:

$$\hat{\pi}_j = \frac{\sum_{i=1}^{n} x_{ij}}{n} \tag{3}$$

$$\hat{\theta}_j = \frac{\sum_{i=n+1}^{n+m} x_{ij}}{m} \tag{4}$$

In the presence of crosstalk, however, it is not possible to compute $\pi$ and $\Theta$ directly from X. A likelihood-based estimation can be used instead.

The log-likelihood of observing the incidence matrix X given the gene expression vector Y is then:

$$\log L = \sum_{i=1}^{n+m} \log(p(X_i | Y_i; \pi_1, \pi_2, \pi_3, \ldots \pi_k, \theta_1, \theta_2, \theta_3 \ldots \theta_k)) \tag{5}$$

Equation 5 is written under the assumption of conditional independence of rows of X; i.e., under the reasonable assumption that the pathway to which a gene i gives most of its impact does not depend on the pathway to which another gene j impacts the most. In other words, the split of the fractions of the impact of a gene does not depend the splits of the impact of other genes.

This assumption, together with the observation that the DE genes do not depend on $\theta$'s and that the NDE genes do not depend on $\pi$'s, allows us to compute the likelihood by separating the matrix in two sub-matrices: X|Y=1, representing the sub-matrix of the DE genes, and X|Y=0, representing the sub-matrix of the NDE genes:

$$\log L = \sum_{i=1}^{n} \log(p(X_i | Y_i = 1, \Pi)) + \sum_{i=n+1}^{m+n} \log(p(X_i | Y_i = 0, \Theta)) \tag{6}$$

$$= \sum_{i=1}^{n} \log(\Pi \cdot X_i') + \sum_{i=n+1}^{m+n} \log(\Theta \cdot X_i')$$

In the following, we will only work with the first term to illustrate how to estimate $\Pi$. $\Theta$ can be estimated from X|Y=0 in a similar fashion.

There is no closed form solution for the maximization of Eq. 6. However, we can use the Z matrix as a hidden variable for the estimation of the parameters $\Pi$. The log joint conditional likelihood for the DE part of the matrix can be written as:

$$\log JL^{DE} = \log(p(X, Z | Y = 1, \Pi)) \tag{7}$$

$$= \sum_{i=1}^{n} \log(p(X_i, Z_i | Y_i = 1, \Pi))$$

$$= \sum_{i=1}^{n} \log(I(Z_i^{DE} \cdot (X_i^{DE})' = 1) \cdot Z_i^{DE} \cdot \Pi)$$

$$= \sum_{i=1}^{n} \log\left((I(Z_i^{DE} \cdot (X_i^{DE})' = 1)) \cdot \sum_{j=1}^{k} Z_{ij}^{DE} \cdot \log(\pi_j)\right)$$

$$= \sum_{i=1}^{n} \log\left(\sum_{j=1}^{k} z_{ij}^{DE} \cdot x_{ij}^{DE}\right) + \sum_{i=1}^{n} \sum_{j=1}^{k} \log(\pi_j) \cdot z_{ij}^{DE}$$

We use an expectation maximization (EM) approach to maximize the log likelihood in Equation 5 by maximizing the joint log likelihood defined in Equation 7. The EM is an iterative algorithm that starts with an initial guess for $\Pi$, denoted with $\Pi^0$; each iteration is a mapping between $\Pi^t$ and $\Pi^{t+1}$. The superscript indicates the index of the iteration. We choose to initialize each element of the vector as follows:

$$\pi_j^0 = \frac{\sum_{i=1}^{n} x_{i,j}}{\sum_{i=1}^{n} \sum_{h=1}^{k} x_{i,h}}, j \in \{1 \ldots k\} \tag{8}$$

This initialization is consistent with the model described in Equation 3.

Each iteration of the EM algorithm is composed by two steps: the expectation step and the maximization step; during the expectation step we compute the expectation of the log joint conditional likelihood in Equation 7 with respect to the posterior $p(Z_{i,j}^{DE} | X_i^{DE}, \Pi^{old})$:

$$E\left(\sum_{i=1}^{n} \log\left(\sum_{j=1}^{k} z_{i,j}^{DE} \cdot x_{i,j}^{DE}\right) + \sum_{i=1}^{n} \sum_{j=1}^{k} \log(\pi_j) \cdot z_{i,j}^{DE}\right) = \tag{9}$$

$$E\left(\sum_{i=1}^{n} \log\left(\sum_{j=1}^{k} z_{i,j}^{DE} \cdot x_{i,j}^{DE}\right)\right) + E\left(\sum_{i=1}^{n} \sum_{j=1}^{k} \log(\pi_j) \cdot z_{i,j}^{DE}\right) =$$

$$E\left(\sum_{i=1}^{n} \sum_{j=1}^{k} \log(\pi_j) \cdot z_{i,j}^{DE}\right)$$

The term $E(\Sigma_{i=1}^{n} \log(\Sigma_{j=1}^{k} z_{i,j}^{DE} \cdot x_{i,j}^{de}))$ is equal to 0 because the term $\Sigma_{j=1}^{k} z_{i,j}^{DE} \cdot x_{i,j}^{DE}$ is equal to 1 for the consistency of Z with X. The derivation of the non zero term of the expectation is as follows:

$$E\left(\sum_{i=1}^{n} \log\left(\sum_{j=1}^{k} z_{i,j}^{DE} \cdot x_{i,j}^{DE}\right)\right) \tag{10}$$

$$\sum_{j=1}^{k} z_{i,j}^{DE} \cdot x_{i,j}^{DE}$$

-continued $$E\left(\sum_{i=1}^{n}\sum_{j=1}^{k}\log(\pi_j)\cdot z_{i,j}^{DE}\right) = \sum_{i=1}^{n}\sum_{j=1}^{k}\log(\pi_j)\cdot E(z_{i,j}^{DE} \mid X_{i,j}^{DE}, \Pi^{old})$$

$$= \sum_{i=1}^{n}\sum_{j=1}^{k}\log(\pi_j)\cdot p(z_{i,j}^{DE}=1 \mid X_i^{DE}, \Pi^{old})$$

$$= \sum_{i=1}^{n}\sum_{j=1}^{k}\log(\pi_j)\cdot \frac{p(z_{i,j}^{DE}, X_i^{DE} \mid \Pi^{old})}{\sum_{r=1}^{k} p(z_{i,j}^{DE}, X_i^{DE} \mid \Pi^{old})}$$

$$= \sum_{i=1}^{n}\sum_{j=1}^{k}\log(\pi_j)\cdot \frac{x_{i,j}^{DE}\cdot \pi_j^{old}}{\sum_{r=1}^{k} x_{i,j}^{DE}\cdot \pi_r^{old}}$$

The maximization of the expectation with respect to $\Pi$, subject to the constraint that $\sum_{j=1}^{k}\pi=1$, is obtained with the Lagrange multiplier method as follows:

$$\sum_{j=1}^{k}\pi_j = 1 \tag{11}$$

$$\frac{d\left[\sum_{j=1}^{k}\log(\pi_j)\sum_{i=1}^{n}\frac{x_{i,h}\cdot \pi_h^{old}}{\sum_{r=1}^{k} x_{i,r}\cdot \pi_r^{old}} + \lambda\left(\left(\sum_{j=1}^{k}\pi_j\right)-1\right)\right]}{d\pi_h} = 0,$$

$\forall h \in \{1 \ldots k\}$ $$\frac{\sum_{i=1}^{n}\frac{x_{i,h}\cdot \pi_h^{old}}{\sum_{r=1}^{k} x_{i,r}\cdot \pi_r^{old}}}{\pi_h} + \lambda = 0, \forall h \in \{1 \ldots k\}$$

We can write a systems of equations over all the possible values of h in order to compute $\lambda$.

$$\begin{cases} \frac{\sum_{i=1}^{n}\frac{x_{i,1}\cdot \pi_1^{old}}{\sum_{r=1}^{k} x_{i,r}\cdot \pi_r^{old}}}{\pi_1} + \lambda = 0 \\ \vdots \\ \frac{\sum_{i=1}^{n}\frac{x_{i,k}\cdot \pi_k^{old}}{\sum_{r=1}^{k} x_{i,r}\cdot \pi_r^{old}}}{\pi_k} + \lambda = 0 \end{cases}$$

$$\begin{cases} \sum_{i=1}^{n}\frac{x_{i,1}\cdot \pi_1^{old}}{\sum_{r=1}^{k} x_{i,r}\cdot \pi_r^{old}} = -\lambda\cdot \pi_1 \\ \vdots \\ \sum_{i=1}^{n}\frac{x_{i,k}\cdot \pi_k^{old}}{\sum_{r=1}^{k} x_{i,r}\cdot \pi_r^{old}} = -\lambda\cdot \pi_k \end{cases}$$

Summing left and right sides we obtain:

$$\sum_{j=1}^{k}\sum_{i=1}^{n}\frac{x_{i,j}\cdot \pi_j^{old}}{\sum_{r=1}^{k} x_{i,r}\cdot \pi_r^{old}} = -\lambda\sum_{j=1}^{k}\pi_j \tag{12}$$

Since $\sum_{j=1}^{k}\pi_j = 1$, we can write:

$$\lambda = -\sum_{j=1}^{k}\sum_{i=1}^{n}\frac{x_{i,j}\cdot \pi_j^{old}}{\sum_{r=1}^{k} x_{i,r}\cdot \pi_r^{old}} \tag{13}$$

We substitute $\lambda$ in 11 and use an iterative process in which a new $\pi$ value is calculated at each step:

$$\frac{\sum_{i=1}^{n}\frac{x_{i,j}\cdot \pi_j^{old}}{\sum_{r=1}^{k} x_{i,r}\cdot \pi_r^{old}}}{\pi_h^{new}} + \lambda = 0, \forall h \in \{1 \ldots k\} \tag{14}$$

$$\frac{\sum_{i=1}^{n}\frac{x_{i,j}\cdot \pi_j^{old}}{\sum_{r=1}^{k} x_{i,r}\cdot \pi_r^{old}}}{\pi_h^{new}} - \sum_{j=1}^{k}\sum_{i=1}^{n}\frac{x_{i,j}\cdot \pi_j^{old}}{\sum_{r=1}^{k} x_{i,r}\cdot \pi_r^{old}} = 0,$$

$\forall h \in \{1 \ldots k\}$ $$\frac{\sum_{i=1}^{n}\frac{x_{i,h}\cdot \pi_h^{old}}{\sum_{r=1}^{k} x_{i,r}\cdot \pi_r^{old}}}{\pi_h^{new}} = \sum_{j=1}^{k}\sum_{i=1}^{n}\frac{x_{i,j}\cdot \pi_j^{old}}{\sum_{r=1}^{k} x_{i,r}\cdot \pi_r^{old}} =,$$

$\forall h \in \{1 \ldots k\}$ $$\pi_h^{new} = \frac{\sum_{i=1}^{n}\frac{x_{i,h}\cdot \pi_h^{old}}{\sum_{r=1}^{k} x_{i,r}\cdot \pi_r^{old}}}{\sum_{j=1}^{k}\sum_{i=1}^{n}\frac{x_{i,j}\cdot \pi_j^{old}}{\sum_{r=1}^{k} x_{i,r}\cdot \pi_r^{old}}}, \forall h \in \{1 \ldots k\}$$

The algorithm stops when the distance between two consecutive vectors $\|\Pi^{(t)}-\Pi^{(t-1)}\|$ is less than the quantity $$\frac{\|\Pi^1 - \Pi^0\|}{100},$$

i.e. the distance between the first two vectors divided by 100. At the end of the steps of the EM algorithm we obtain the matrix C from which we can obtain the most probable Z given the condition under study: for each row, we assign the value 1 to the cell with the highest probability, and 0 to all the others. This is equivalent to saying that each gene gives its full impact to the pathway with the highest $\pi$ value.

Choice for the Threshold for the Module Detection Procedure.

The value 0.25 for the module selection procedure was selected by calculating all modules for all data sets with different thresholds in the [0, 0.4]range (with a difference of 0.025 between thresholds). The results are shown in FIG. 19. As it can be seen in the figure, the number of modules found in all data sets shows a plateau in the [0.1, 0.375] range.

The disclosed techniques may be implemented using a suitably programmed computer having associated machine-readable memory for storing program instructions and data used in the disclosed computations. In one embodiment the disclosed computations may be programmed using the R statistical computing and graphics software environment available from www.r-project.org. Other statistical modeling tools, such as Mathematica and Matlab or other programming environments such as Java or C++ may also be used.

What is claimed is:

1. A computer-implemented method of correcting for crosstalk effects in analyzing a set of reference pathways and a list of genes or proteins or metabolites or reactants that are differentially expressed in a given condition, comprising:

constructing, via a computer, a matrix whereby each pathway to which any given gene or protein or metabolite or reactant contributes most is identified;

processing, via said computer, the matrix by applying a likelihood-based estimation upon an impact matrix and thereby identify a new set of new and/or existing pathways that is not affected by crosstalk effects;

generating, via said computer, a heat map using the matrix, the heat map illustrating a p-value of each pathway when an influence of genes or proteins or metabolites or reactants from each other pathway are removed;

displaying, via said computer, the heat map; and treating a patient based on the heat map.

2. The method of claim 1 wherein the likelihood-based estimation includes performing expectation maximization.

3. The method of claim 1 further comprising performing module detection by identifying sub-pathways that have an apparent role in to the given condition, but independent of the pathway to which they belong.

* * * * *